United States Patent [19]

Saljoughian et al.

[11] Patent Number: 6,160,128
[45] Date of Patent: Dec. 12, 2000

[54] TRITIOACETYLATING REAGENTS AND PROCESSES FOR PREPARATION THEREOF

[75] Inventors: Manoucher Saljoughian, Moraga; Hiromi Morimoto, El Cerrito; Philip G. Williams, Oakland; Chit Than, Lafayette, all of Calif.

[73] Assignee: The Regents of the University of California, Oakland, Calif.

[21] Appl. No.: 09/177,882

[22] Filed: Oct. 23, 1998

Related U.S. Application Data

[60] Provisional application No. 60/068,398, Dec. 22, 1997.
[51] Int. Cl.[7] .................................................. C07D 207/40
[52] U.S. Cl. ........................... 548/545; 548/473; 548/475
[58] Field of Search .................................... 548/545, 473, 548/475

[56] References Cited

PUBLICATIONS

1992 Aldrich Catalog, Aldrich Chemical Company, Milwaukee, WI, p. 708, 1992.

Baschang et al. J. Labelled Compd. Radiopharm., 20:691–696, 1983.

Manouchehr Saljoughian, et al., N Tritioacetoxyphalimide: A New Specific Activity Tritioacetylating Reagent, *The Journal of Organic Chemistry*, 9625–9628, vol. 61, No. 26 (Dec. 22, 1996).

Manouchehr Saljoughian, et al, New Tritium Labelling Reagents And Techniques, Abstracts of Papers, American Chemical Society, 074, 212th ACS National Meeting, Orlando, Florida (Aug. 25–29, 1996).

Manouchehr Saljoughian et al, Continuing Education, International Isotope Society, Final Program and Abstracts, A17, (May 16–17, 1996).

Hiromi Morimoto et al, What's New At The NTLF?, International Isotope Society, Ninth Central U.S. Meeting, (Jun. 6 & 7, 1996).

Hendrik Andres, et al, Seven Years Exploration of New Tritium Labelling Methods, International Isotope Society, Fifteenth Northeast U.S. Meeting, Oct. 24&25, (1996) Mystic, Connecticut.

Alexander Hampton, et al, Evidence for Species–Specific Substrate–Site–Directed Inactivation of Rabbit Acetylate Kinase by $N^6$–(6–Iodoacetamido–nhesyl) adenosine 5'Triphosphate, vol. 19, No. 11, 1279–1283, *Journal of Medicinal Chemistry* (1976).

Edward Grochowski, et al, A New Method For The PReparation of N acyloxyphthalimides and N–Acyloxysuccinimides, Synthesis 277–279, Communications (Apr. 1977).

Chit Than, et al, Preparation, NMR Characterization, and Labeling Reactions of Tritiated Borane–THF Complex at High Specific Radioactivity, 7503–7507, *The Journal of Organic Chemistry*, vol. 60 (1995).

D. G. Lindsay et al, The Acetylation of Insulin, *Biochem. J.*, 121:737–745, (1971).

N. de Groot, et al, The Synthesis of N–Acetylphenylalanyl–sRNA, *Biochemical and Biophysical Research Communications*, vol. 25, No. 1, pp. 17–22, (1966).

*Primary Examiner*—James O. Wilson
*Assistant Examiner*—Howard Owens
*Attorney, Agent, or Firm*—Hana Verny

[57] ABSTRACT

Novel acetylating and tritioacetylating reagents suitable for preparation of nonlabelled and radiolabelled organic compounds. N-acetoxynaphthalimide, N-tritioacetoxyphthalimide, N-tritioacetoxysuccinimide, N-tritioacetoxynaphthalimide and processes of their preparation. The invention also concerns synthesis of nonlabelled acetylated and tritioacetylated organic compounds from precursors containing a free —$NH_2$, —SH or —OH group.

34 Claims, 9 Drawing Sheets

CHLOROFORM SOLVENT

TRITIOACETYLATING REAGENTS AND PROCESSES FOR PREPARATION THEREOF

This Application is based on Provisional Application Ser. No. 60/068,398 filed on Dec. 22, 1997.

The United States Government has certain rights in this invention pursuant to Contract DE-AC03-76SF00098 between the United States Department of Energy and the University of California.

BACKGROUND OF THE INVENTION

1. Field of the Invention

This invention concerns new acetylating and tritioacetylating reagents. In particular this invention concerns acetylating reagent N-acetoxynaphthalimide and tritioacetylating reagents N-tritioacetoxyphthalimide, N-tritioacetoxysuccinimide, and N-tritioacetoxynaphthalimide, as well as processes for their preparation. These reagents are useful for preparation of nonlabelled acetylated compounds and for preparation of acetylated organic compounds radiolabelled with high tritium content. The invention also concerns a method for synthesis of nonlabelled acetylated and tritioacetylated organic compounds from precursors containing a free —$NH_2$, —SH or —OH group.

2. Background and Related Disclosures

Acetylated and particularly tritiolabelled acetylated organic compounds with high radiolabel content are in high demand. However, their availability and cost depends on available methods for their preparation. While both the acetylating reagents and tritiolabelled compounds are currently available, their cost is high and, in the case of tritiolabelled compounds, the tritium content is typically rather low, which limits their utility.

Therefore, it would be advantageous to have available new methods and reagents for simplified preparation of acetylated organic compounds and for preparation of acetylated tritiolabelled compounds with high tritium content.

The available methods for preparation of acetylated compounds have been shown to be either relatively non-specific, as these reagents may react with other functional groups present in organic compounds, or require multi-step manipulations, non-ambient incubations, other complex reaction conditions and typically afford low yield. All these conditions lengthen the time of and raise the cost of preparation of acetylated compounds such as acetyl Co-enzyme A, acetylcholine, acetylated amino acids or other acetylated organic compounds.

Exemplary of the problems occurring with preparation of acetylated and tritioacetylated compounds is the preparation of acetyl Co—A. The major routes currently used for the production of acetyl Co—A are enzymatic systems or systems utilizing specialty usually high cost reagents. The most commonly used enzyme for the synthesis of acetyl Co—A is acyl co-enzyme A synthetase (ACS). Additionally, the chemical synthesis of acetyl Co—A may employ acetylating reagents such as thioacetate, acetic anhydride, (*J. Am. Chem. Soc.,* 75:2520 (1952)) sodium acetate, (*Anal. Biochem.,* 176:82 (1989) and ibid, 224:159 (1995)), and S-acylthiocholine iodide (*J. Org. Chem.,* 56:3752 (1991)). The disadvantages of the currently available methods, as described in *J. Org. Chem.* 56:3752 (1991), include low yield, lengthy preparation, high cost of reagents such as ACS, lack of purity and the contamination of products with lipids present in the enzyme preparations.

Some attempts have been made to rectify these problems. For example, activated imido ester compounds which are highly reactive at 0° C. have been reported as useful N-acylating reagents, as described in *J. Am. Chem. Soc.,* 83:1263 (1961), and ibid, 86:1839 (1964).

N-acetoxyphthalimide was used to prepare N-acetylmuramic acid, as described in *J. Org. Chem.,* 30:448 (1963), and N-iodoacetoxysuccinimide was used for iodoacetylation of $N^6$-(6-amino-n-hexyl)adenosine-5'-phosphate, as described in *J. Med. Chem.,* 19:1279 (1976).

The limitations of preparation of tritiated acetylated compounds utilizing tritiated acetic anhydride and tritiated acetic acid as acetylating reagents are well known and, as indicated in *Br. J. Nutr.,* 68:365 (1992), include low tritium content, volatility, and poor chemical selectivity. The tritiated acetyl derivatives produced by the acetylating methods described above can be produced only at a very low specific activity and their usefulness is therefore limited (*Biochem. J.,* 121:737 (1971)).

Attempts to prepare acetylated tritiated compounds include a reaction of [$^{14}$C]phenylalanyl-s-RNA with N-acetoxysuccinimide and N-tritioacetoxysuccinimide, *Biochem. Biophys. Res. Commun.,* 25:17 (1966). N-tritioacetoxysuccinimide, at 0.6 Ci/mmole, was used to tritioacetylate insulin according to *Biochem. J.,* 121:737 (1971); a high specific activity tritioacetyl group was made by iodoacetylation of muramyl dipeptide with N-iodoacetylsuccinimide, and subsequent catalytic tritiodehalogenation (*J. Label. Compd. Radiopharm.,* 20:691 (1983)). As an alternative to acetylation, N-Succinimidyl [2,3-$^3$H]propionate at very high specific activity has been used to acylate proteins, as described in *Science,* 208:303 (1980), but such propionylation resulted in appreciable loss of biological activity, as suggested in *J. Biol. Chem.,* 255:3575 (1980), is ineffective in the presence of stabilizing thiols, as indicated in *J. Label. Compd. Radiopharm.,* 20:277 (1983), or requires long reaction times (ibid, 31:459 (1992)).

Therefore, it would be desirable to develop new and more efficient acetylating and tritioacetylating reagents and processes for preparation of nonlabelled acetylated compounds and tritiolabelled acetylated compounds with high tritium content.

A primary aim of this invention is thus to develop non-volatile, stable and facile acetylating and tritioacetylating reagents having demonstrable utility for synthesis of nonlabelled acetylated compounds and tritioacetylated organic compounds from precursors containing a free —$NH_2$, —SH or —OH group.

Accordingly, this invention describes a preparation of a novel acetylating reagent, N-acetoxynaphthalimide, useful for preparation of nonlabelled acetylated compounds, and a preparation of tritioacetylating reagents, N-tritioacetoxyphthalimide, N-tritioacetoxysuccinimide and N-tritioacetoxynaphthalimide, having a high tritium content useful for preparation of the tritiolabelled acetylated compounds. The invention also describes methods for preparation of acetylated organic compounds from precursors containing free —$NH_2$, —SH or —OH groups, including amino acids, peptides, Co—A, choline.

All patents, patent applications and publications cited and referred to herein are hereby incorporated by reference.

SUMMARY OF THE INVENTION

One aspect of the current invention is an acetylating reagent N-acetoxynaphthalimide useful for preparation of acetylated compounds.

Another aspect of the current invention is a tritioacetylating reagent selected from the group consisting of N-tritioacetoxyphthalimide, N-tritioacetoxysuccinimide or N-tritioacetoxynaphthalimide useful for labelling of organic compounds with tritium.

Still yet another aspect of the current invention is a process for preparation of N-tritioacetoxyphthalimide, N-tritioacetoxysuccinimide or N-tritioacetoxynaphthalimide.

Still yet another aspect of the current invention is a process for preparation of N-tritioacetoxyphthalimide, N-tritioacetoxysuccinimide or N-tritioacetoxynaphthalimide, comprising synthesis of these reagents from their iodo-precursor by reduction with tributyltin tritide in a radical dehalogenation reaction.

Yet another aspect of the current invention are the tritiolabelling reagents containing one, two or three tritium atoms.

Still another aspect of the current invention is N-ditritioacetoxyphthalimide, N-tritritioacetoxyphthalimide, N-ditritioacetoxysuccinimide, N-tritritioacetoxysuccinimide, N-ditritioacetoxynaphthalimide and N-tritritioacetoxynapthalimide.

Still yet another aspect of the current invention is a method for synthesis of $^3$H acetoxyphthalimide reagent using trimethylsilylacetoxyphthalimide.

BRIEF DESCRIPTION OF DRAWINGS

FIG. 6 shows the NMR spectra of $^3$H acetyl derivative of a peptide made up of seven amino acids in $D_2O$.

DEFINITIONS

Figure 1:
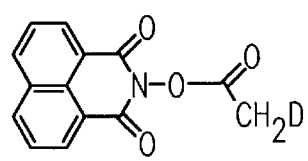
FIG. 1 shows the $^2$H NMR spectrum of N-deuterioacetoxynaphthalimide in chloroform, synthesized by radical dehalogenation.
Figure 1:
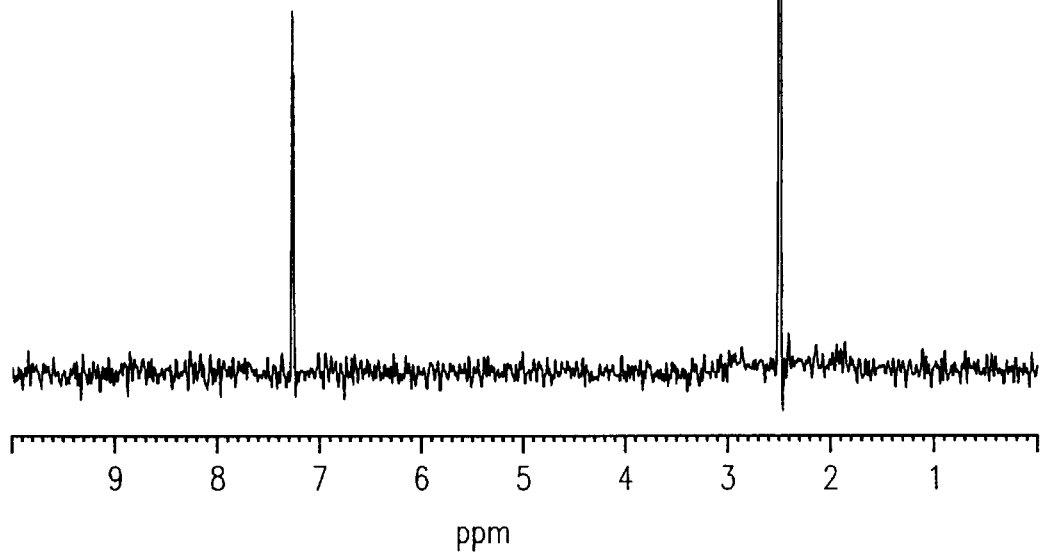

As used herein:

"Lower alcohol" means alcohol, preferably a primary alcohol, containing from 1 to 6 carbons, selected from the group consisting of methanol, ethanol, propanol, isopropanol, butanol, isobutanol, t-butanol, hexanol and heptanol.

"Reaction solvent" means tetrahydrofuran (THF), ethyl acetate (EtOAc), dimethylsulfoxide (DMSO), acetone, acetonitrile (ACN), dioxane, triethylamine, tetrahydrofuran (THF) and the like, and mixtures thereof.

"HT", "$H^3H$", "$T_2$" or "$^3H$—$^3H$" means tritium gas.
"Analog" means naphthalimide or succinimide analog of phthalimide.

"Precursor" means phthalimide, succinimide, naphthalimide, or iodo or bromoacetoxy derivative thereof. These compounds are precursors for tritiated N-acetoxyphthalimide, N-acetoxysuccinimide and N-acetoxynaphthalimide.

"Tritium analog" means N-ditritio or N-tritritio derivatives of N-tritioacetoxyphthalimide, N-tritioacetoxysuccinimide and N-tritioacetoxynaphthalimide.

"Halo" means Cl, I, or Br.

DETAILED DESCRIPTION OF THE INVENTION

This invention concerns novel acetylating reagent and novel tritioacetylating reagents of high specific activity and processes for their preparation.

The invention additionally concerns a method for facile chemical synthesis of acetylated organic compounds from precursors containing free —$NH_2$, —SH or —OH groups, such as CoA, choline, benzylamine, amino acids and peptides. The products may be unlabelled or labelled with tritium. The method is fast and easy and results in a high yield of synthesized nonlabelled acetylated compounds or tritiated acetylated compounds having a high content of tritium.

Accordingly, this invention discloses an acetylating reagent N-acetoxynaphthalimide and a process for its preparation, and tritioacetylating reagents N-tritioacetoxyphthalimide, N-ditritioacetoxyphthalimide, N-tritritioacetoxyphthalimide, N-tritioacetoxysuccinimide, N-ditritioacetoxysuccinimide, N-tritritioacetoxysuccinimide, N-tritioacetoxynaphthalimide, N-ditritioacetoxynaphthalimide and N-tritritioacetoxynaphthalimide having a high tritium content and a process for their preparation, said process comprising synthesis of the tritiated reagents from their halo-precursors by reduction with tributyltin tritide in a radical dehalogenation reaction.

Additionally, the invention discloses an alternate process for preparation of acetylating reagent N-acetoxyphthalimide using trimethylsilylacetoxyphthalimide as a precursor.

All reagents and processes for their preparation and uses, as well as methods for preparation of acetylated and tritioacetylated organic compounds from precursors containing free —$NH_2$, —SH or —OH groups, including Co—A, choline, benzylamine, amino acids and peptides, described herein, and any modification of general character are intended to be within the scope of this invention.

I. Acetylating and Tritioacetylating Reagents

I.A. Acetylating Reagents

Three types of acetylating reagents were prepared. These reagents were N-acetoxyphthalimide, N-acetoxysuccinimide and N-acetoxynaphthalimide.

I.A.1. General Considerations

Selection factors for preparation of each acetylating reagent included ease of synthesis and quantification of the acetoxy precursors, and solubility and reactivity of the acetylating reagents in various solvent mixtures. Based on these considerations, three acetoxy precursors were selected, namely phthalimide, succinimide and naphthalimide.

I.A.2. Characteristics

Succinyl and phthalyl derivatives showed equal ease of synthesis. Phthalyl and naphthyl derivatives were easier to quantify than succinyl. Succinyl and phthalyl were equally reactive but naphthyl was less reactive.

Overall, N-acetoxyphthalimide was the preferred acetylating reagent because it is readily synthesized, has excellent reactivity, solubility and chromatographic characteristics.

I.A.3. Acetylation Reactions

Acetylation reactions utilizing acetylating reagents of the invention were investigated on organic molecules containing amino ($-NH_2$) groups, such as peptides, benzylamine, amino acids, ACTH, muramic acid, cysteine and neurotensin; and hydroxyl group ($-OH$), such as Choline; and sulfhydryl group ($-SH$), such as CO-enzyme A.

Appropriate solvents for acetylation reactions were as defined, with preferred solvents acetonitrile, DMSO, dioxane, a primary alcohol and THF.

The N-acetylation method is exemplified by the acetylation of an $-NH_2$ containing organic compound using N-acetoxynaphthalimide, shown in Scheme 1.

SCHEME 1

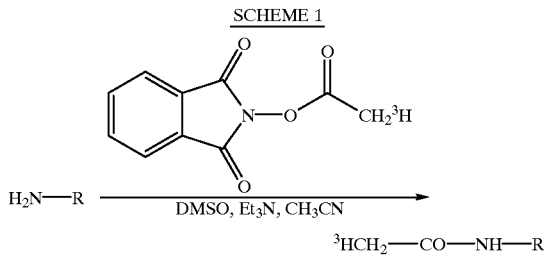

wherein R is a peptide, amino acid or other organic molecule residue containing a free $-NH_2$ group.

As seen in Scheme 1, N-acetylation proceeds in an organic solvent or a mixture thereof, as defined, preferably acetonitrile, DMSO and triethylamine for amino group containing organic compounds.

Hydroxyl or thiol containing compounds are acetylated in a very similar manner.

I.A.4. Reaction Speed and Specificity

The acetylating reactions using the acetylating reagents of the invention are rapid and specific. The reaction requires only a mild temperature, preferably room temperature, and is very rapid, resulting in a yield of over 80% of the product after 15 minutes. The reaction is very specific. For example, one equivalent of N-acetoxyphthalimide with one equivalent of cysteine yields only N-acetyl cysteine. Use of two equivalents of the reagent with one equivalent cysteine yields N,S-di acetyl cysteine.

I.B. N-Tritioacetylating Reagents

Three types of tritioacetylating reagents were prepared. The reagents were N-tritioacetoxyphthalimide, N-tritioacetoxysuccinimide and N-tritioacetoxynaphthalimide, or their N-ditritio or N-tritritio analogs.

I.B.1. General Considerations

Selection factors for preparation of tritioacetylating reagents included ease of synthesis and quantification of the halo-acetoxy precursors, and their ease of tritiation and purification.

I.B.2. Characteristics

For the preparation of N-tritioacetylating reagents, acetylating reagents described above were halogenated with bromo or, preferably, with iodo and tritiated with one, two or three tritium atoms (T).

All three halo-acetoxy precursors, bromo or iodoacetoxyphthalimide, bromo or iodoacetoxysuccinimide and bromo or iodoacetoxynaphthalimide were found to be readily synthesized. These precursors were then converted either by catalytic dehalogenation, or preferably, by radical dehalogenation to tritioacetylating reagents. Synthesis of the precursors is described in Example 3.

I.B.3. Tritiation of Halo-Acetoxy Precursors

Preparation of halo-acetoxy precursors and catalytic dehalogenation using $D_2$ gas is illustrated in Scheme 2.

Catalytic dehalogenation using HT gas is described in detail in Example 4.

SCHEME 2

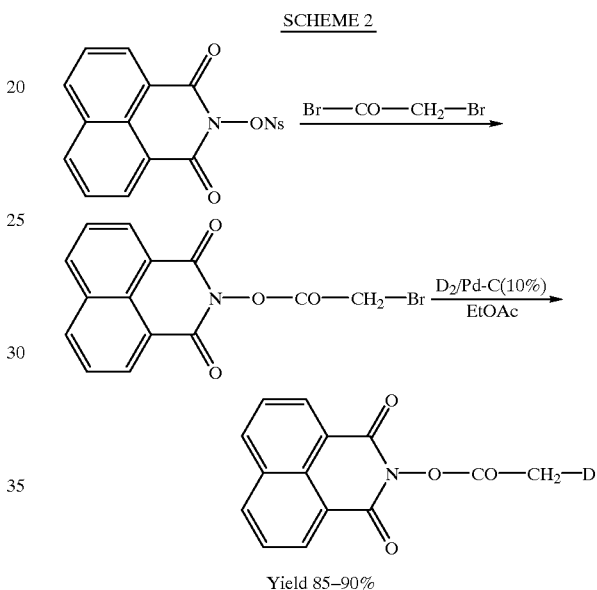

Yield 85–90%

Scheme 2 illustrates synthesis of N-bromoacetoxynaphthalimide used for catalytic dehalogenation. The catalytic dehalogenation reaction proceeds in the presence of palladium on carbon catalyst, preferably 10% Pd-C, in an organic solvent as defined, preferably ethyl acetate, in the presence of $D_2$ gas, under mild reaction conditions, such as room temperature. The catalytic dehalogenation reaction is relatively slow, yielding around 80–90% of the product. However, catalytic dehalogenation is not able to meet the primary objective of this invention, that is to provide acetylating reagents with high radiolabel content. Tritiation of bromoacetoxynaphthalimide in the same way yielded 85% radiochemical yield, but a low specific activity of 0.5 Ci/mmole.

Catalytic dehalogenation for preparation of tritiated compounds is illustrated in Scheme 3. Scheme 3 shows synthesis of N-iodoacetoxysuccinimide and its conversion via catalytic dehalogenation into N-tritioacetoxysuccinimide.

SCHEME 3

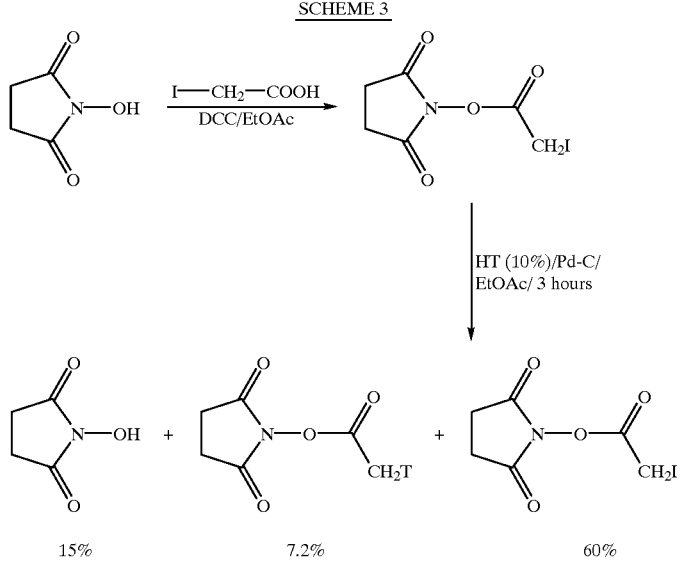

As seen in Scheme 3, N-hydroxysuccinimide is coupled with iodoacetic acid in the presence of dicyclohexylcarbodiimide into N-iodoacetoxysuccinimide, which is then subjected to catalytic dehalogenation in the presence of tritium gas. A catalytic dehalogenation reaction using iodo acetoxysuccinimide in the presence of 10% palladium on carbon and 10% tritium in hydrogen run for 3 hours resulted in only about 7% radiochemical yield, representing a very low tritium incorporation into the acetoxy group.

Because the catalytic dehalogenation was relatively slow and yields only low specific activity compounds, the new method wherein the catalytic dehalogenation is replaced with radical dehalogenation was developed and is described herein.

In the preferred radical dehalogenation, N-tritioacetylating reagents were prepared by radical dehalogenation of N-iodoacetoxyphthalimide, N-iodoacetoxysuccinimide and N-iodoacetoxynaphthalimide using high specific activity tributyltin tritide according to Scheme 4.

SCHEME 4

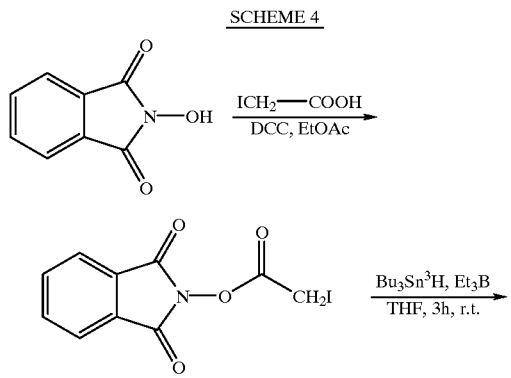

-continued

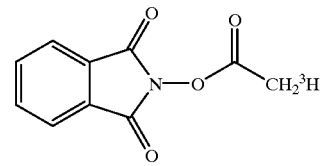

Radical dehalogenation is described in Example 5.

According to the method shown in Scheme 4, the tritioacetylating reagent N-tritioacetoxyphthalimide, or N-tritioacetoxysuccinimide or N-tritioacetoxynaphthalimide is conveniently synthesized from the iodo-precursor by reduction with tributyltin tritide in a radical dehalogenation reaction yielding a compound with specific activity of more than 14 Ci/mmole.

The resulting tritioacetylating reagent is highly reactive towards α-amino, hydroxyl and sulfhydryl groups in proteins or other organic compounds, and exhibits rapid acetylation activity when reacted in the presence of water and an organic solvent, as defined, and a lower alcohol, as defined.

Figure 5:
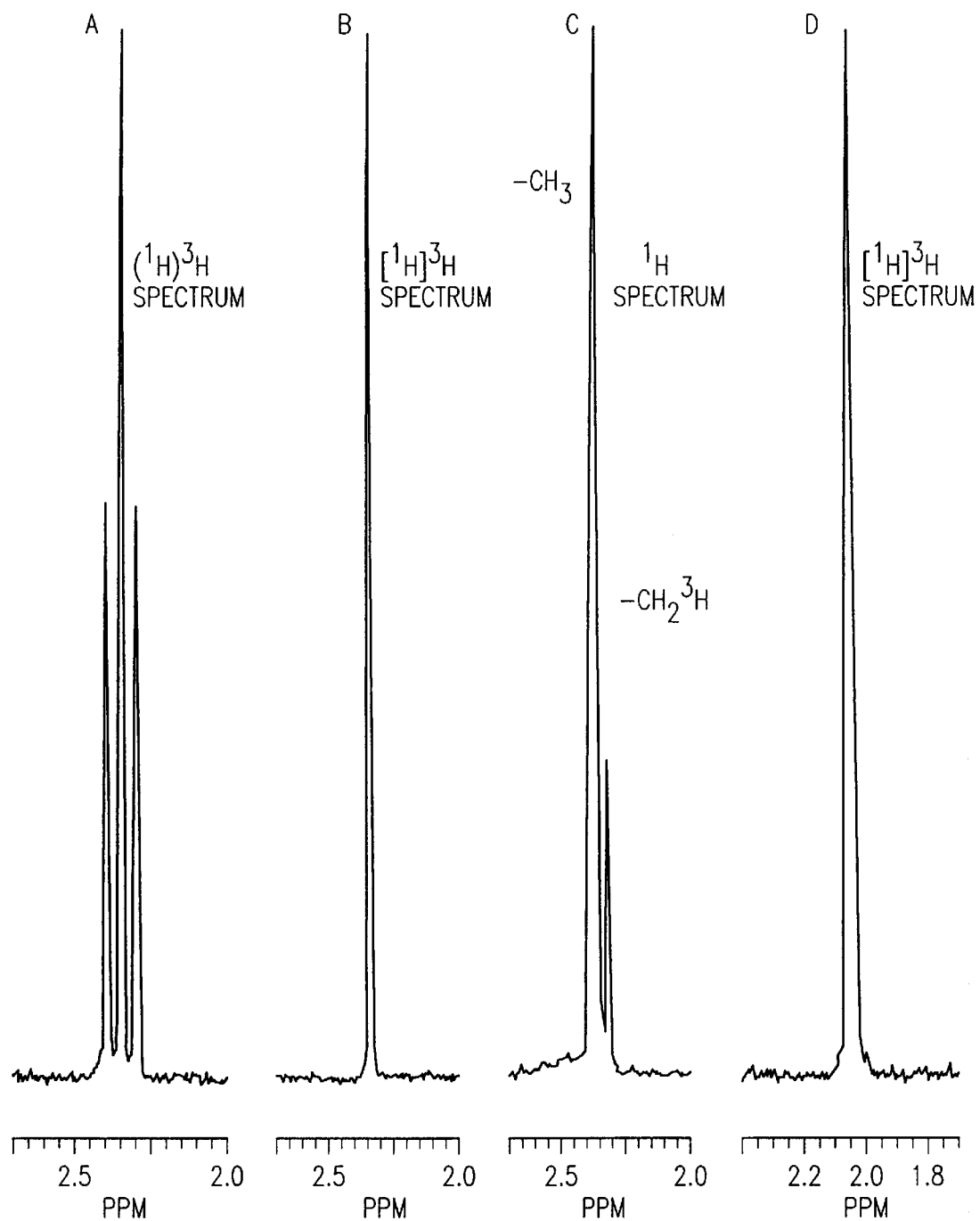
FIG. 5 shows the $^3$H and $^1$H NMR spectra of N-tritioacetoxyphthalimide and N-tritioacetyl-ACTH.

FIG. 5 shows the NMR spectra of the acetoxy product of radical-induced reactions.

I.B.4. Specific Tritioacetylating Reagents

Three specific tritioacetylating reagents were prepared using radical dehalogenation. Of the three reagents, N-tritioacetoxyphthalimide provided the highest yield and particularly highest tritium content. This reagent is therefore particularly preferred.

The maximum theoretical S.A. obtainable with one tritium atom per molecule is about 28.76 Ci/mmole. Consequently, where one tritium atom per molecule is used, the maximum S.A. is 28.76 Ci/mmole, when two tritium atoms per molecule are used, the S.A. of the resulting compound is 57.5 Ci/mmole and when three tritium atoms are used, S.A. is 86.3 Ci/mmole.

I.C. N-tritioacetoxyphthalimide

A preferred tritioacetylating reagent, N-tritioacetoxyphthalimide of high specific radioactivity (S.A.) of about 1 to about 87 Ci/mmole, preferably 5 to about 28.7 Ci/mmole, was prepared as described in Example 5.

Two batches of tritioacetoxyphthalimide were prepared, and separated from their by-products by extraction with acetonitrile and hexane. Radio HPLC, proton and tritium NMR analysis of the purified product revealed a radiochemically pure reagent with chemical yields of 38 and 40% and specific activities of 13 and 18 Ci/mmole.

I.D. N-Ditritio and N-Tritritioacetoxyphthalimides

The radical dehalogenation approach has been used to prepare N-dideuterioacetoxyphthalimide (Scheme 5). An analogous approach with tritium would yield N-ditritioacetoxyphthalimide. A different method is used for the synthesis of N-tritritioacetoxyphthalimide (Scheme 6). Detailed description of the preparation of N-ditritio or N-tritritioacetoxy reagents is found in Example 13.

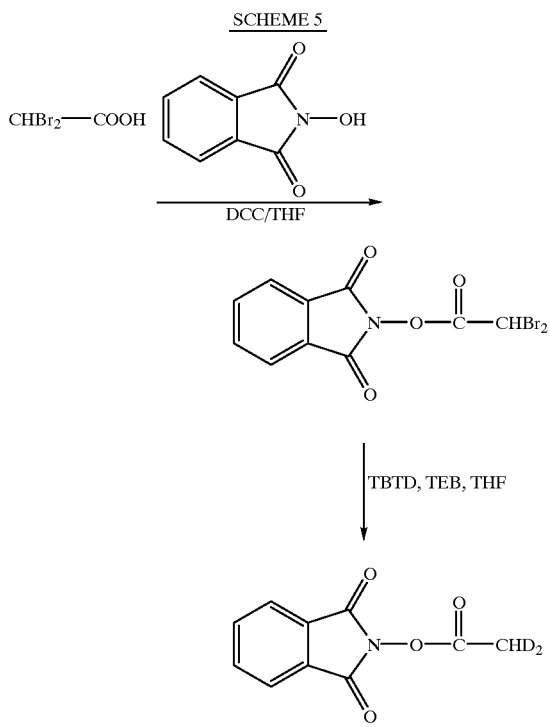

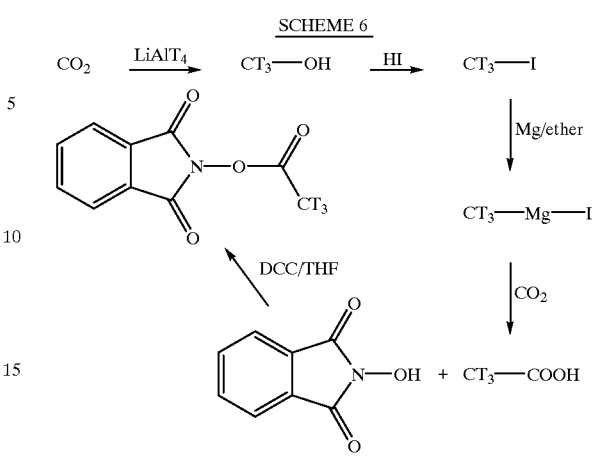

Scheme 6 illustrates preparation of N-tritritioacetoxyphthalimide. N-tritritioacetoxyphthalimide is prepared from high specific activity tritiated methyl iodide through tritiated methyl magnesium iodide, which when reacted with carbon dioxide results in release of tritiated acetic acid. High specific activity tritiated acetic acid is reacted with N-hydroxyphthalimide in the presence of DCC.

The tritiated methyl iodide may be prepared by the reduction of $CO_2$ with $LiAlT_4$. The $LiAlT_4$ may be prepared by the method of Andres et al. described in *J. Chem. Soc., Chem. Commun.*, 627 (1990). The tritiated methyl iodide can also be prepared from tritiated methanol at 100% isotopic abundance, which, in turn, can be prepared from catalytic reduction of $CO_2$ with tritium gas by the method of Ott, et al, described in *J. Label. Compounds*, 10, p. 315 (1974). The reaction seen in Scheme 6 illustrates the N-tritritio reagent labelled with three tritium atoms having a specific activity up to about 87 Ci/mmole.

Ditritio- or tritritioacetylating analogs may be prepared in the same way.

New tritioacetoxy reagents N-tritioacetoxyphthalimide, N-tritioacetoxysuccinimide, N-tritioacetoxynaphthalimide and their di- and tri-tritiated analogs of high specific activity (1–87 Ci/mmole) are disclosed. The reagents are solid, nonvolatile and stable compounds which require 1–1.5 equivalents for complete acetylation. The new reagents are highly reactive to all amino, hydroxyl and sulfhydryl groups, and exhibit acetylating activity in the presence of organic solvents, alcohols, and water.

Reaction of the tritioacetylating reagents of the invention with a peptide or other organic compound possessing $NH_2$, —SH or —OH groups results in acetylating the organic compound and tritiolabelling it with an unusually high specific activity never before achieved.

I.E. N-Tritioacetoxysuccinimide Reagent

The tritioacetylating agent N-tritioacetoxysuccinimide has high reactivity with proteins and other organic molecules and may be conveniently, easily and quickly tritiated to specific activity above 10 Ci/mmole.

For preparation of N-dideuterioacetoxyphthalimide, dihaloacetic acid, such as dibromoacetic, dichloroacetic acid or diiodoacetic acid is contacted with N-hydroxyphthalimide in the presence of an organic solvent as defined, preferably THF, in the presence of DCC for about 2 hours. The obtained N-dibromoacetoxyphthalimide is subjected to radical dehalogenation with tributyltin deuteride resulting in the doubly deuteriated reagent. N-ditritioacetoxythalimide can be prepared the same way using tributyltin tritide.

Figure 2:
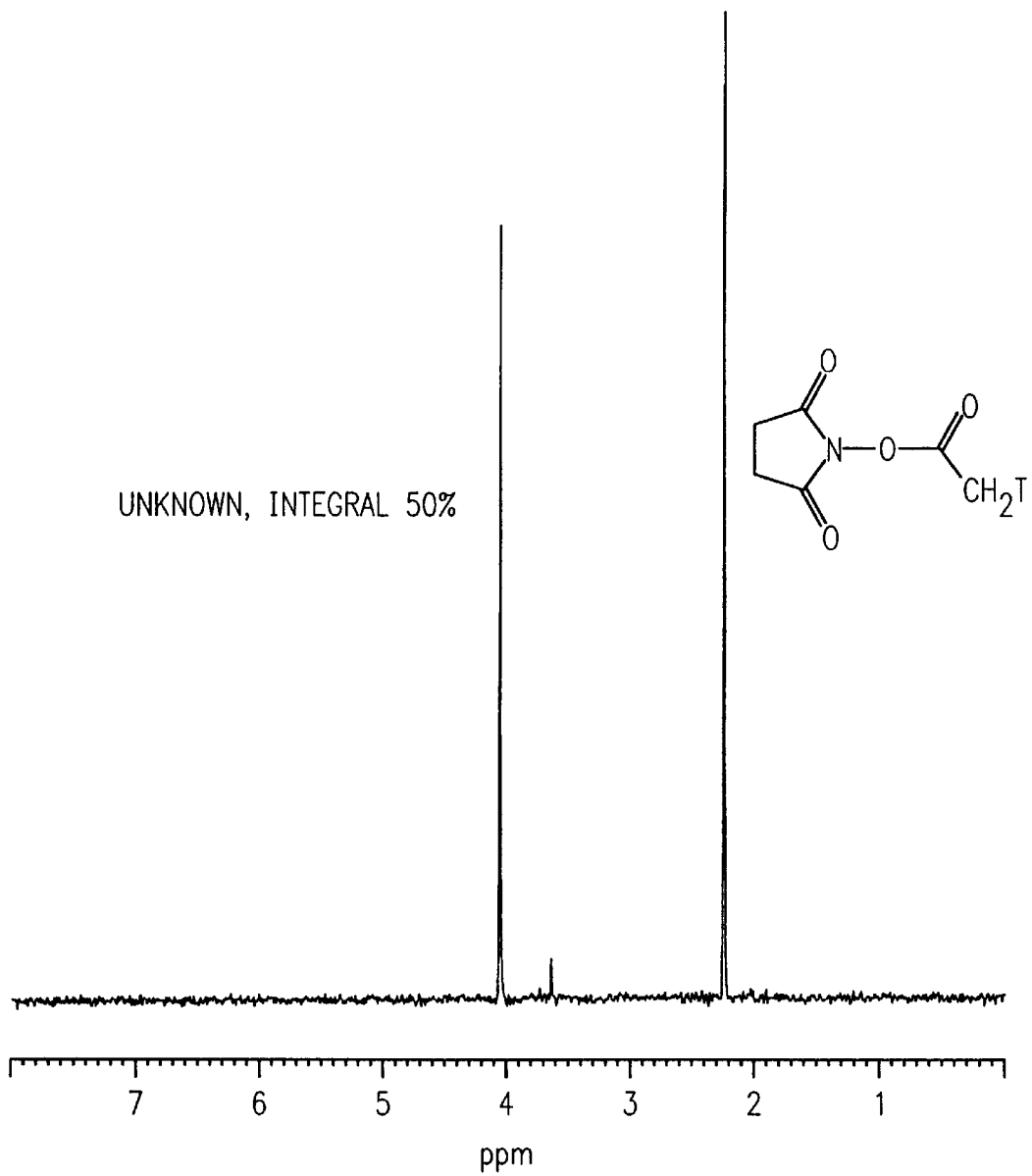
FIG. 2 shows the $^3$H NMR spectrum of N-tritioacetoxysuccinimide in tetrahydrofuran, synthesized by catalytic dehalogenation.

N-tritioacetoxysuccinimide is prepared according to Example 4. NMR spectrum of N-tritioacetoxysuccinimide in tetrahydrofuran prepared by catalytic dehalogenation is seen in FIG. 2.

N-Ditritioacetoxysuccinimide and N-tritritioacetoxysuccinimide may be prepared according to schemes 5 and 6, respectively, substituting N-hydroxyphthalimide with N-hydroxysuccinimide.

I.F. N-Tritioacetoxynaphthalimide Reagent

The tritioacetylating reagent, namely N-tritioacetoxynaphthalimide, of specific activity between about 1 and 87 Ci/mmole is conveniently prepared according to Scheme 7 and Examples 4 or 5.

SCHEME 7

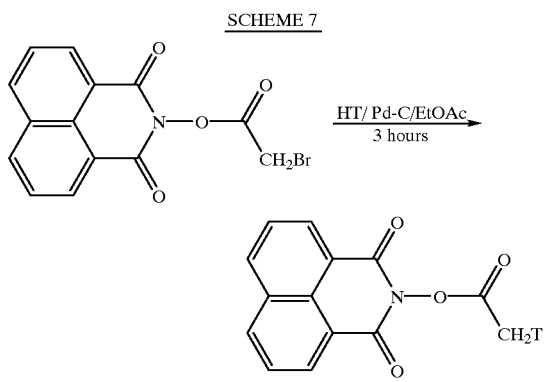

Figure 3:
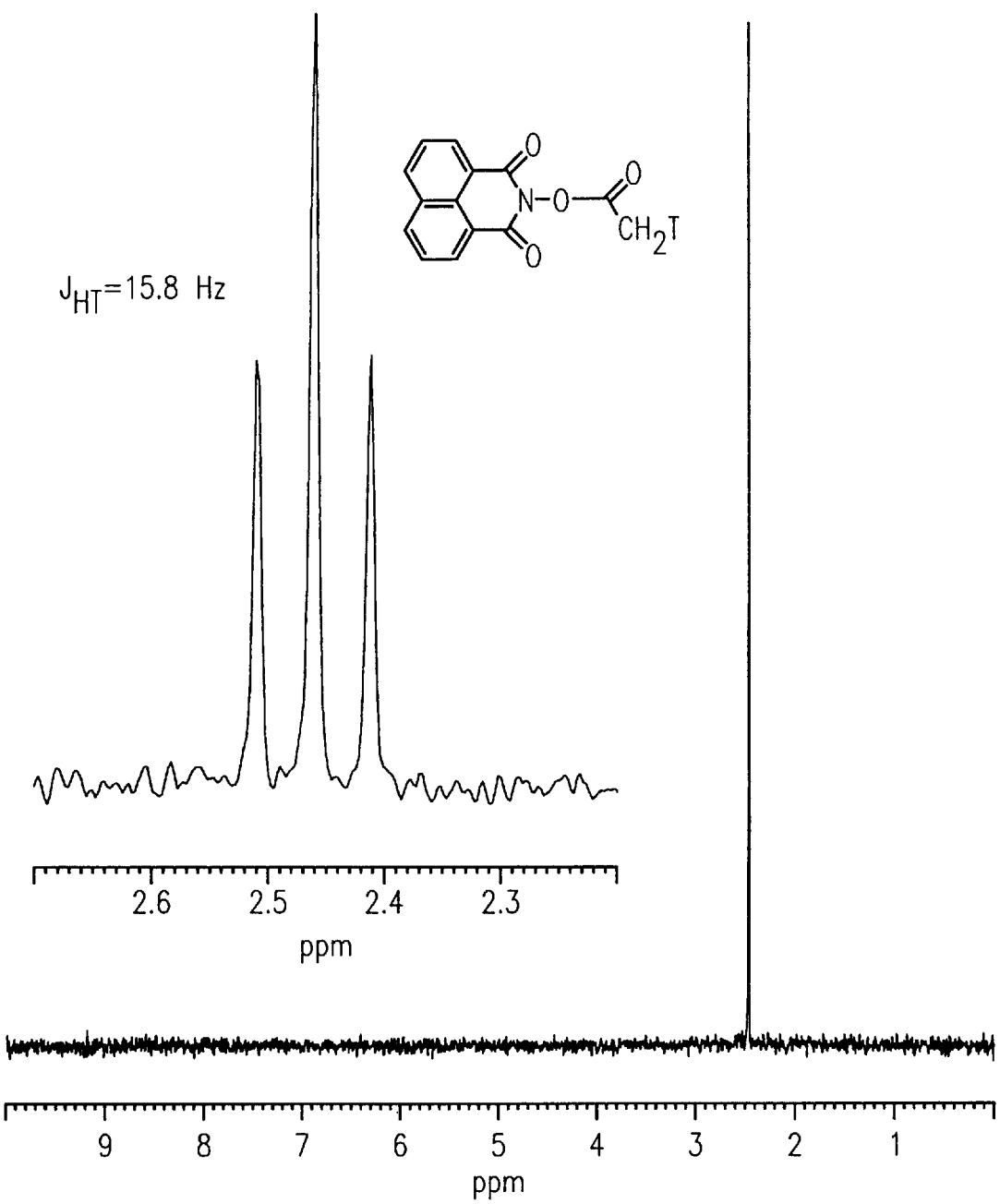
FIG. 3 shows the $^3$H NMR spectra of N-tritioacetoxynaphthalimide in $CDCl_3$ prepared by catalytic dehalogenation.

Scheme 7 illustrates preparation of N-tritioacetoxynaphthalimide by catalytic dehalogenation. N-bromoacetoxynaphthalimide is treated with tritiated gas in the presence of Pd-C catalyst to provide N-tritioacetoxynaphthalimide reagent. Reaction is fast and has a yield of above 85%. NMR spectra of N-tritioacetoxynaphthalimide is seen in FIG. 3.

The N-tritioacetoxynaphthalimide has a good reactivity with proteins.

N-Ditritioacetoxynaphthalimide and N-tritritioacetoxynaphthalimide may be prepared according to schemes 5 and 6, respectively, substituting N-hydroxyphthalimide with N-hydroxynaphthalimide.

The tritioacetylating reagents of the invention, as described above, are solid, non-volatile and stable compounds and normally 1 to 1.5 equivalents of the reagent affords rapid and complete tritioacetylation. The easy preparation of the reagents, their use and analysis makes them very attractive for synthesis of compounds of high specific activity and superior as tritioacetylating reagents to either tritiated acetic anhydride or tritiated acetic acid used previously.

The N-acetoxyphthalimide was found to be most readily synthesizable, have excellent reactivity, solubility, and chromatographic characteristics and is therefore the most preferred tritioacetylating reagent.

II. Radical Dehalogenation for Preparation of Tritioacetylating Reagents

Previously available methods for preparation of tritiated acetylating compounds had generally very low specific activity. One of these methods is catalytic dehalogenation. In order to improve the isotope incorporation and to obtain a reagent of high specific activity, the prior catalytic dehalogenation approach was replaced with radical dehalogenation.

This process allows preparation of high specific activity N-tritioacetoxy and N-ditritiacetoxy reagents, prepared from N-iodo or N-bromoacetoxyphthalimide, N-iodo or N-bromoacetoxysuccinimide and N-iodo or N-bromoacetoxynaphthalimide using high specific activity tributyltin tritide (TBT$^3$H).

Generally, N-tritioacetoxyphthalimide, N-tritioacetoxysuccinimide or N-tritioacetoxynaphthalimide, is prepared by reaction of N-hydroxyphthalimide, succinimide or naphthalimide with iodoacetic or bromoacetic acid in the presence of dicyclohexylcarbodiimide, and dry organic solvent, preferably ethyl acetate. Compounds are reacted under these conditions for about 1 to 6, preferably 3 hours, at a temperature from about 15 to about 25° C., preferably at room temperature, to produce the N-iodoacetoxy or N-bromoacetoxy precursor, which, in turn, is reacted with tributyltin tritide and triethylborane used as the radical initiator in a dry organic solvent, preferably tetrahydrofuran, for about 1 to 6 hours, preferably 3 hours, at temperature from about 15 to about 25° C., preferably at room temperature.

Each tritioacetylating reagent obtained as seen in Scheme 4, above, is characterized by $^3$H and $^1$H NMR spectroscopy and by radio-HPLC. Efficacy of the reagent is investigated by tritioacetylation of several peptides at their N-terminal amino groups, hydroxyl or sulfhydryl acetylations.

III. Preparation of N-Tritioacetoxyphthalimide by Fluoride-Induced Tritiodesilylation Reaction An alternative way of preparing N-tritioacetoxyphthalimide reagent is a fluoride-induced tritiodesylation reaction.

Fluoride ion is known to display a marked nucleophilic affinity for silicon in organosilanes. Thus, the generation of carbanions from organosilanes with strong silophiles such as fluoride ion is a facile synthetic reaction. In this process, the carbanion is trapped with an electrophile (e.g. proton) via a fluorodesilylation reaction.

The desilylation reaction avoids harsh reaction conditions, does not utilize tin and consequently does not result in tin contaminated reagent, and can proceed in the presence of sensitive electrophiles, substrates or products.

This method has been modified to utilize $T_2O$ as the electrophile, cesium fluoride as the nucleophile and N-trimethylsilylacetoxyphthalimide as a substrate for the fluoride-induced desilylation reaction.

The fluoride-induced tritiodesilylation reaction is illustrated in reaction Scheme 8 and described in Example 7.

SCHEME 8
Fluoride-Induced Tritiodesilylation

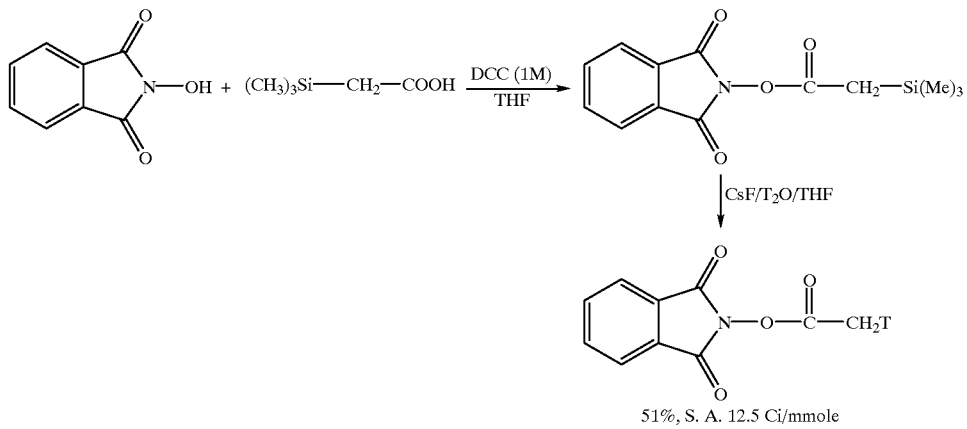

51%, S. A. 12.5 Ci/mmole

To obtain N-tritioacetoxyphthalimide by tritiodesylilation, N-trimethylsilylacetoxyphthalimide was prepared from N-hydroxyphthalimide and trimethylsilyl acetic acid by a coupling reaction using DCC/THF under very dry conditions, as described in Example 7. The coupling reaction was followed by addition of the nucleophile, preferably cesium fluoride, and a final quench by $T_2O$ according to Scheme 8. The obtained N-tritioacetoxyphthalimide had a high specific activity of 12.5 Ci/mmole and a yield of about 51%.

The method's additional advantages are prevention of the early formation of side products during the synthesis and avoidance of contamination of the final product with the by-products dicyclohexylurea and tin. The method thus results in a cleaner product with higher chemical yield than the radical dehalogenation method.

The above described fluoride-induced tritiodesilylation reaction is an alternative method for preparation of N-tritioacetoxyphthalimide, N-tritioacetoxysuccinimide and N-tritioacetoxynaphthalimide reagents.

IV. Acetylation and Tritioacetylation Reactions

The acetylation and tritioacetylation capability of the acetylating and tritioacetylating reagents of the invention and the methods for acetylation and tritioacetylation were investigated and confirmed on various peptides, amino acids, and other organic molecules containing amino, hydroxy and thiol groups.

IV.A. Acetylation of Organic Compounds

Acetylation of compounds such as muramic acid (Scheme 9), benzylamine (FIG. 4 and Scheme 10), and L-cysteine (Scheme 11), is performed using the reagents, as defined, and alcohols, as defined, and water, according to the method of the invention.

SCHEME 9

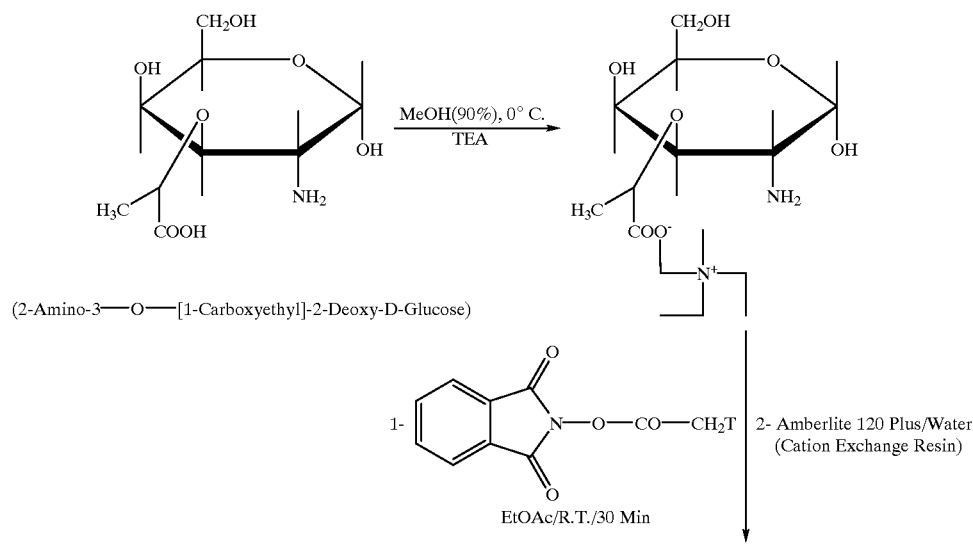

(2-Amino-3—O—[1-Carboxyethyl]-2-Deoxy-D-Glucose)

1- EtOAc/R.T./30 Min

2- Amberlite 120 Plus/Water (Cation Exchange Resin)

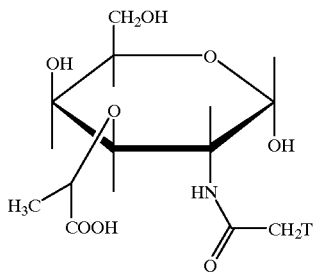

Scheme 9 illustrates acetylation of muramic acid containing an —NH$_2$ group. Muramic acid (2-amino-3-0-[1-carboxyethyl]-2-deoxy-D-glucose), was reacted with N-tritioacetoxyphthalimide in the presence of organic solvent, as defined, at room temperature for about 30 minutes. The free NH$_2$ group of muramic acid was N-tritioacetylated as seen in Scheme 9.

Scheme 10 illustrates acetylation of benzylamine.

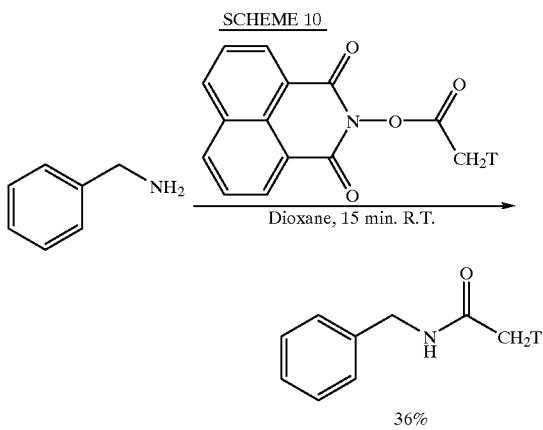

Figure 4:
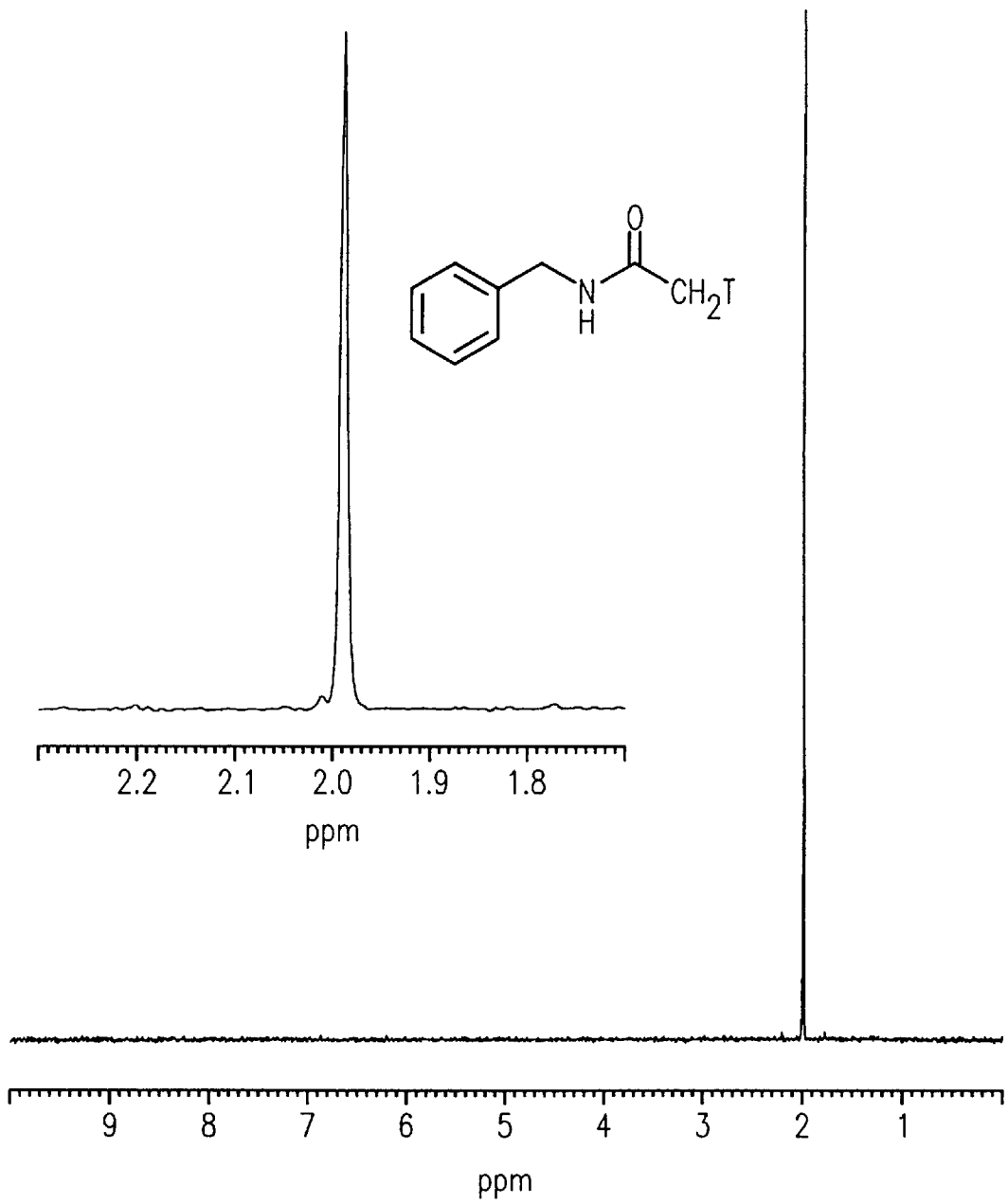
FIG. 4 shows the $^3$H NMR spectrum of N-tritioacetylbenzylamine in $CDCl_3$.

Benzylamine is acetylated, preferably in the presence of dioxane, for about 15 minutes at room temperature. The reaction yields almost 85% of the acetylated benzylamine. FIG. 4 shows NMR spectra of N-tritioacetylbenzylamine: 320MH$_z$ $^3$H NMR spectrum of [$^3$H] acetylbenzylamine δ (CDCl$_3$) 2.00 (S, N—CO—CH$_2$T).

Acetylation of cysteine is shown in Scheme 11. Cysteine was reacted with N-acetoxynaphthalimide in the presence of the organic solvent, as defined, preferably dioxane, at room temperature. The reaction was very fast, in about 15 minutes over 85% of cysteine was acetylated.

SCHEME 11

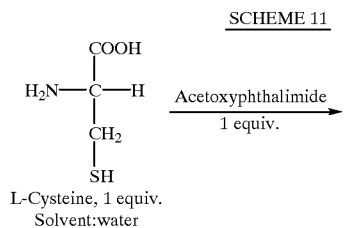

L-Cysteine, 1 equiv.
Solvent:water

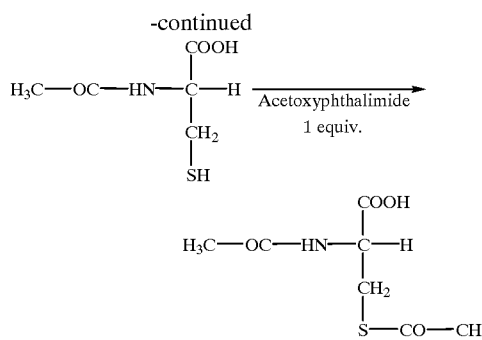

When 1 equivalent of L-cysteine in water is acetylated with 1 equivalent of N-acetoxyphthalimide in acetonitrile, N-acetyl-L-cysteine was generated as the sole product, as shown by NMR and mass spectrometric analyses (1:1; reagent:substrate, N—(C=O)—CH$_3$ $^1$H NMRδ (D$_2$O) 2.05). Use of 2 equivalents of the N-acetoxy-phthalimide reagent under the same reaction conditions generated N,S-diacetyl-L-cysteine. (2:1; reagent:substrate, N—(C=O)—CH$_3$ $^1$H NMRδ (D$_2$O) 2.05(s); S—(C=O)—CH$_3$ 2.36(s).

When the above mentioned compounds were acetylated according to the invention, acetylation was both rapid and specific.

IV.B. Tritioacetylation of Organic Compounds

The tritioacetoxy reagents were used to N-tritioacetylate ACTH, neurotensin and several other peptides.

For tritioacetylation, high specific activity tritioacetylating reagents are prepared as described above, and then reacted with a protein, peptide, amino acid or other organic compound substrate to be tritioacetylated.

The generic tritioacetylation process is illustrated in Scheme 1, above.

The tritioacetylations of specific organic compounds are carried out by reacting tritioacetylating reagent, such as N-tritioacetoxyphthalimide, dissolved in an organic solvent, as defined, and added to a solution of a substrate, in ratio of about 1:1 of the reagent to the organic substrate, such as protein, peptide or amino acid, typically in DMSO or other organic solvent, as defined, under mildly basic conditions, as described fully in the examples.

Two peptides, ACTH and neurotensin were tritioacetylated according to the method of the invention. Results of their radio-HPLC, proton ($^1$H) and tritium ($^3$H) NMR analyses revealed radiochemically pure products.

The tritium NMR spectra of the reaction products showed a single peak at 2.02 ppm for the N-[$^3$H]-acetylated ACTH at the N-terminal serine and a single peak at 2.03 ppm for N-[$^3$H]-acetylated neurotensin at the N-terminal arginine with specific activities of 18 Ci/mmole and 13 Ci/mmole, respectively. The chemical yields of about 33% to 37% of N-tritioacetyl products were determined by radio-HPLC, starting from the batches of tritiated reagent with specific activities of 18 and 13 Ci/mmole.

The applicability of the reagents for N-tritioacetylation reactions was further demonstrated with the labelling of six different peptides containing from 6 to 17 amino acid residues, prepared by solid-phase techniques as described in Examples 8 and 9. An additional result is seen in FIGS. 6A–C.

In contrast to the two examples given above, the C-terminus of each peptide was still attached to a hydroxymethyl resin (HMP) and all amino acid side chains were protected, with only the N-terminus free for acetylation. In this instance, after N-tritioacetylation, the peptides were released from the resin, deprotected, and purified by radio-HPLC to be used in a peptide precipitation assay. The peptide with the highest specific activity, having specific activity of about 17 Ci/mmole was additionally analyzed by tritium NMR spectroscopy and showed a singlet at 2.04 ppm, corresponding to the N-tritioacetyl group attached to the N-terminal amino acid (FIG. 6).

Figure 6A:
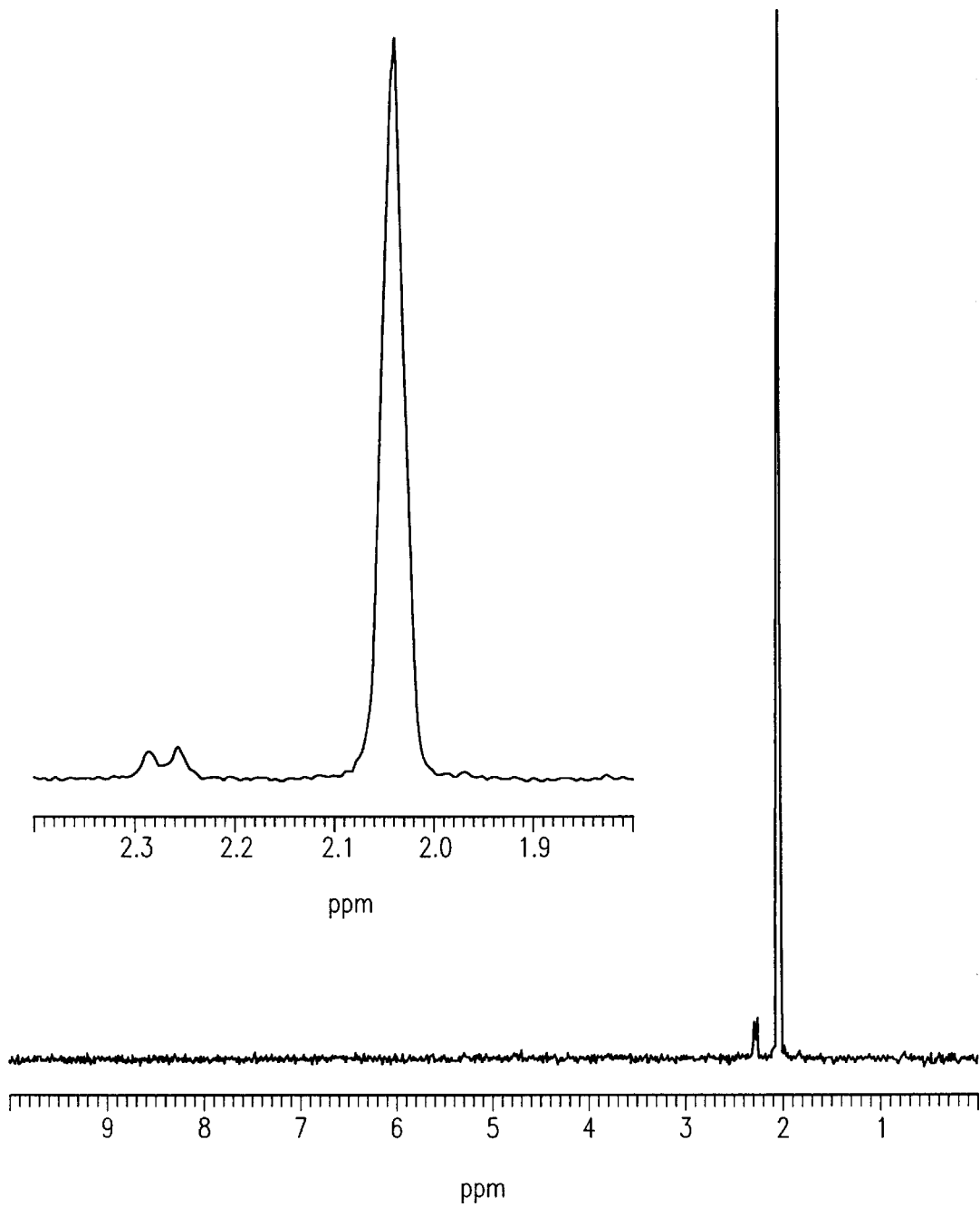
FIG. 6A shows the 320 $MH_z$ $^3$H NMR spectrum of the [$^3$H]acetyl derivative of the above peptide.
Figure 6B:
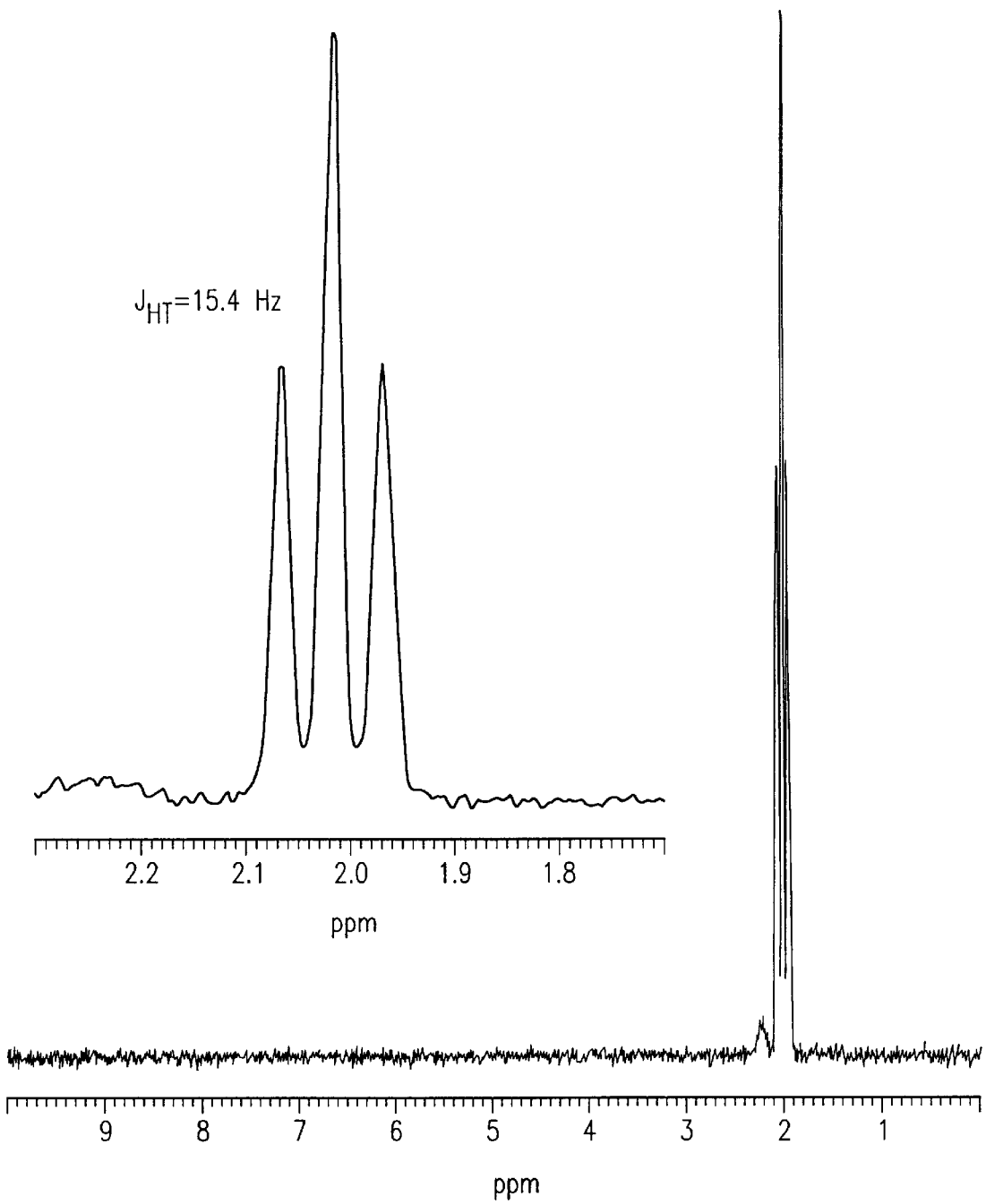
FIG. 6B shows the $^1$H coupled $^3$H NMR spectrum. δ ($D_2O$) 2.14(t). $J_{HT}$=16$H_z$.
Figure 6C:
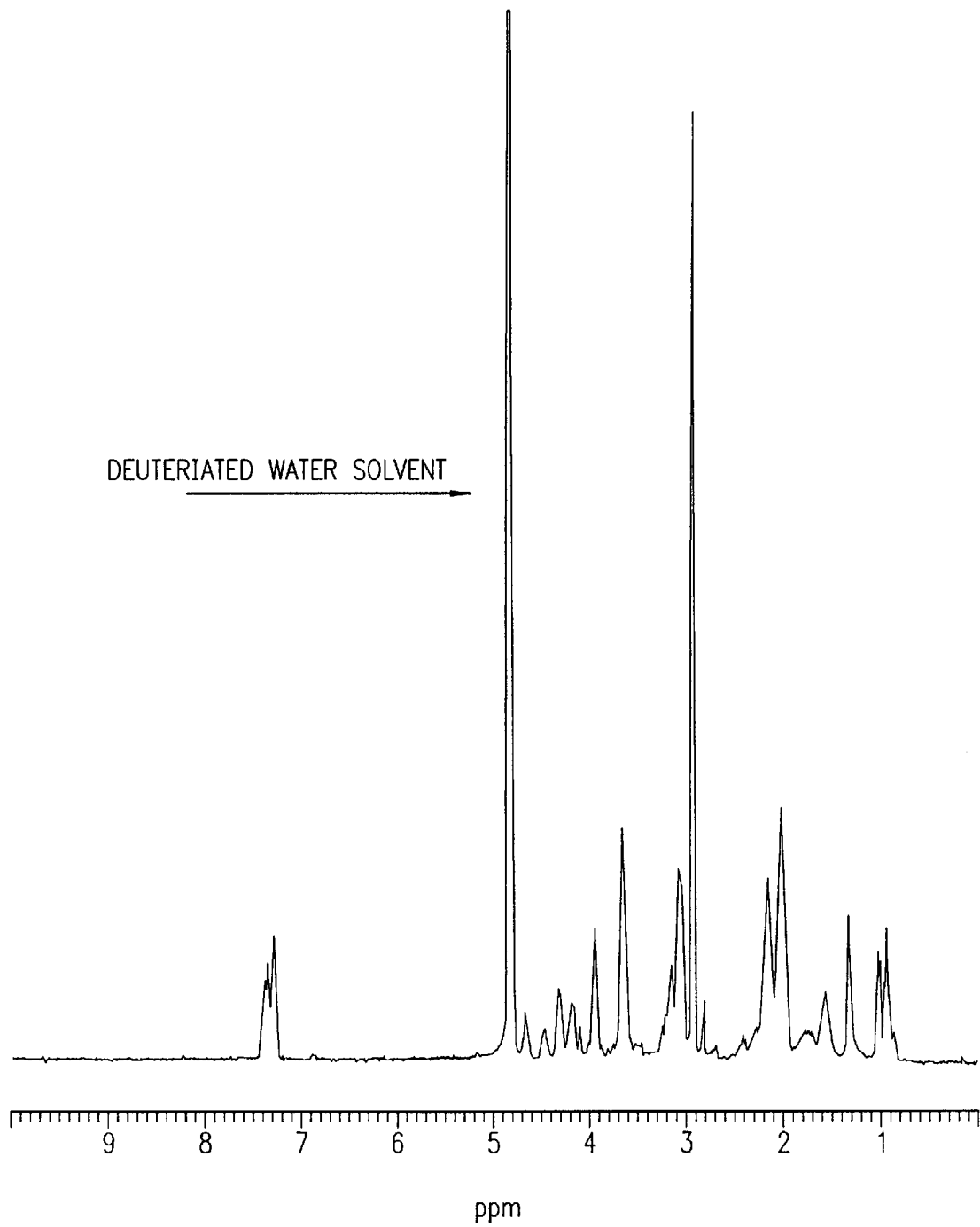
FIG. 6C shows the 300 $MH_z$ $^1$H NMR spectrum of the peptide in $D_2O$.

FIG. 6A shows 320 MH$_z$ $^3$H NMR spectrum of [$^3$H]acetyl derivative of a peptide containing seven amino acids. FIG. 6B shows $^1$H coupled $^3$H NMR spectrum. δ (D$_2$O) 2.14(t). J$_{HT}$=16H$_z$. FIG. 6C shows 300 MH$_z$ $^1$H NMR spectrum of the peptide in D$_2$O.

The above described results clearly demonstrated the utility of the invention for rapid acetylation and acetylation coupled with tritiolabelling of organic compounds. The identity, synthesis and use of N-tritioacetoxyphthalimide and its analogs having a high specific activity as new and selective reagents for the facile tritium labelling and acetylation of peptides and other molecules containing free—NH$_2$, —OH or SH groups was thus discovered, tested, demonstrated and their tritioacetylating capability confirmed.

IV.C. Chemical Synthesis of Acetyl Co—A and High Specific Activity [$^3$H] Acetyl Co—A A very important and specific use of the invention is its utility for preparation of tritiolabelled and nonlabelled acetylated compounds such as acetyl Co—A and acetylcholine. The new and facile acetylation method of the invention enables the acetylation of Co-enzyme A using N-acetoxyphthalimide or its analogs as the acetylating reagents. The reaction is very suitable for preparation of these compounds because it is performed and proceeds under very mild conditions.

Acetyl Co—A was selectively prepared by the acetylation of the terminal sulfhydryl group of co-enzyme A in water under mild basic conditions using N-acetoxyphthalimide as described in Example 10. The S-acetylated product so obtained was analyzed by HPLC and $^1$H NMR spectroscopy.

Tritiated acetyl Co-enzyme A was prepared in the same fashion using the tritiolabelling method with a tritiolabelling reagent. The tritiolabelling method is shown in Scheme 12. The method is a simple and efficient microscale procedure for the chemical synthesis of high specific activity [$^3$H] acetyl co-enzyme A (Example 11), utilizing N-tritioacetoxyphthalimide, N-tritioacetoxysuccinimide or N-tritioacetoxynaphthalimide, or the di- or tritritio analogs, as shown in Scheme 12.

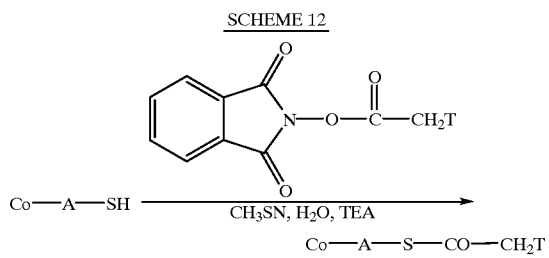

SCHEME 12

The reaction of N-tritioacetoxyphthalimide with specific activity of 18 Ci/mmole with the sodium salt of co-enzyme A in water generated the corresponding tritiated [$^3$H]acetyl co-enzyme A under the same reaction conditions as those used for preparation of unlabelled acetyl Co—A.

$^1$, H $^3$H NMR spectroscopy and radio-HPLC was used to determine the specificity of tritium labelling, specific activity and radiochemical purity of the S-tritioacetylated product. These methods confirmed that the resulting compound was $^3$H-acetyl Co—A having specific activity 14.4 Ci/mmole. Proton and tritium NMR analyses of the purified tritiated acetyl-CoA is shown in FIG. 7.

Figure 7:
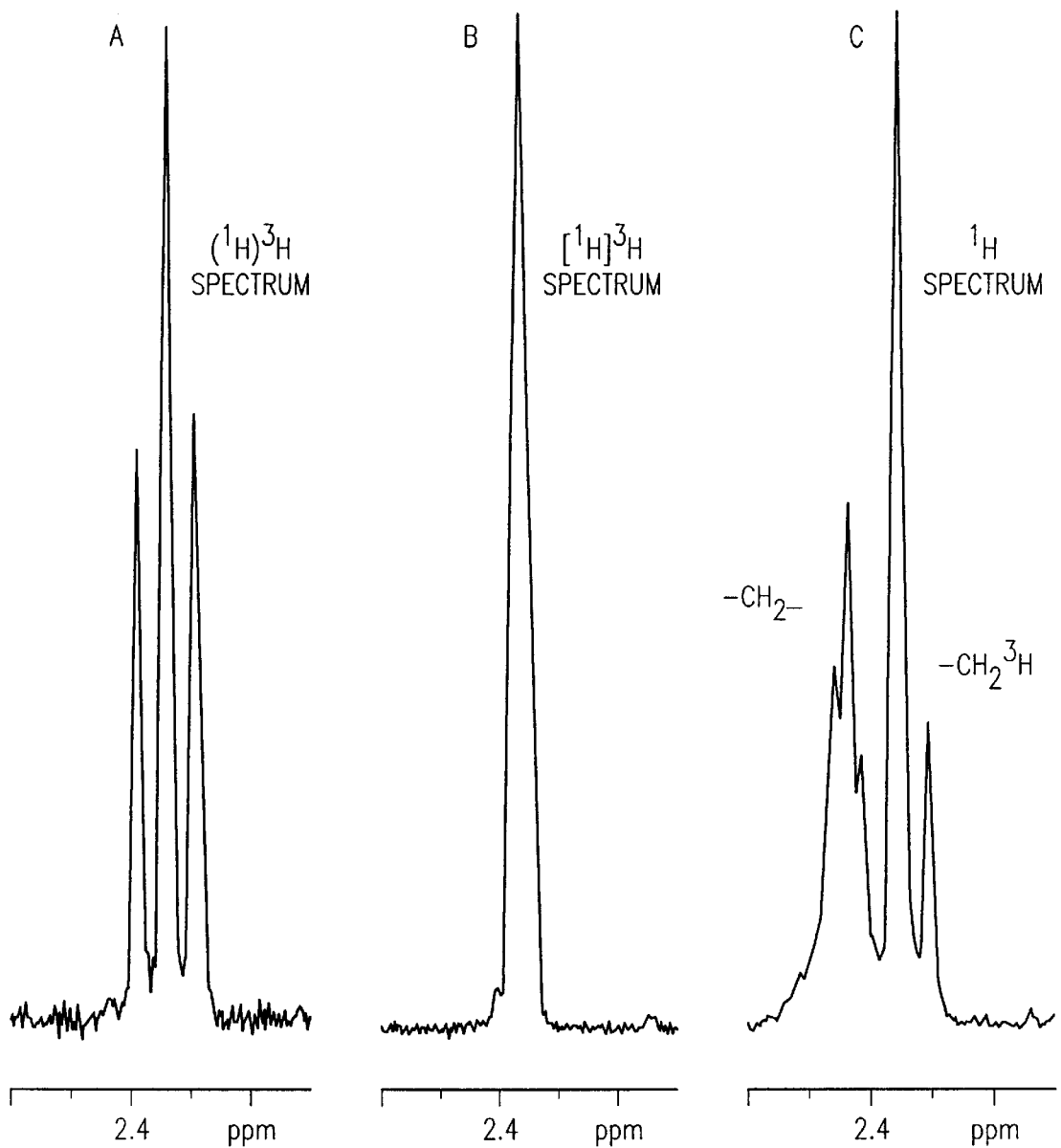
FIG. 7 shows $^3$H and $^1$H NMR spectra of N-tritioacetoxyphthalimide in deuteriated acetylnitrile and N-tritioacetyl Co—A in $D_2O$.

The results seen in FIG. 7 reveal radiochemically pure [$^3$H]acetyl Co-enzyme A. The tritium NMR spectrum of the product showed a triplet for the proton coupled tritium spectrum, as seen in FIG. 7A (J$_{HT}$ 15.60 Hz), and a singlet $^1$H decoupled $^3$H at 2.35 ppm in deuterated water for the S-tritioacetyl group, as seen in FIG. 7B. As seen in FIG. 7C, the proton NMR spectrum of the tritiated sample showed a singlet for the —CH$_3$ species at 2.35 ppm and one line from the doublet for —CH$_2$T species at 2.30 ppm. The downfield line of the doublet is obscured by the singlet of the —CH$_3$ species. The specific radioactivity of the [$^3$H]acetyl Co-enzyme A after purification was determined by analysis of the proton NMR spectrum of the tritiated sample and found to be 14.4 Ci/mmole. This value represents six times higher specific activity than any tritiolabelling of this compound previously available.

Previous methods allowed preparation of tritiated [$^3$H] acetyl Co—A at a specific activity of only up to 2.28 Ci/mmole. Acetyl Co-enzyme A synthetase was used to prepare [$^3$H]acetyl co-enzyme A from Co-enzyme A and [$^3$H]sodium acetate in a reaction which is costly, lengthy and difficult.

Although [$^3$H]acetyl Co-enzyme A having a specific activity of 2–10 Ci/mmole or [$^3$H]sodium acetate having a specific activity of 2–10 Ci/mmole are commercially available, these chemicals have a lower specific activity than the compound prepared according to the invention and are very expensive.

Compared to previously available methods, the current method thus provides improved, fast, high yield synthesis of tritiated acetyl Co—A having a high tritium content (14.4 Ci/mmole or more).

This method was demonstrated as a new, facile and cost-effective microscale procedure. Compared with prior existing enzymatic methods, the current chemical preparation of [$^3$H]acetyl Co-enzyme A and its analysis is superior. The method is inexpensive, has high yield of about 80% and provides acetyl Co—A of higher chemical and radiochemical purity.

IV.D. Tritiolabelling of Acetylcholine

Acetylcholine is a very important pharmacological agent which is widely utilized for pharmacokinetic, pharmacological and neurochemical studies. For these purposes, the labelled acetylcholine is often necessary.

Tritiosynthesis of $^3$H-acetylcholine according to the invention is illustrated in Scheme 13.

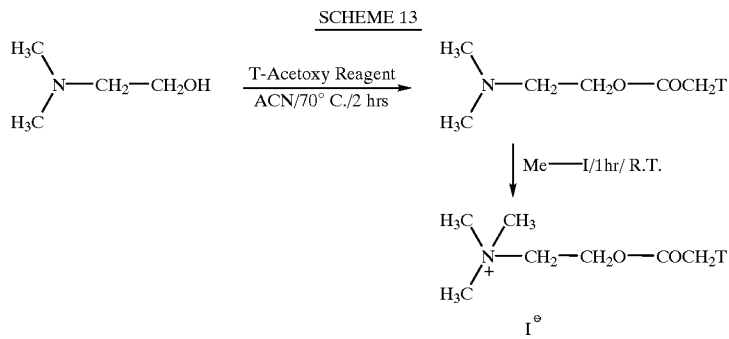

SCHEME 13

The detailed tritiosynthesis of acetylcholine is described in Example 12 and involves dissolving a primary alcohol, such as N,N-dimethylamino ethanol in an amount from about 0.04 mmole to about 40 mmoles in about 0.25 to about 2.5 mL of an organic solvent, as defined, preferably acetonitrile, and reacting the mixture with N-tritioacetoxyphthalimide or other tritioacetylating reagent having specific activity of at least 13 Ci/mmole, also dissolved in an organic solvent, preferably acetonitrile in amount from about 0.8 to about 8 mL. Acetylation occurs in acetonitrile without the addition of any organic base such as triethylamine, typically used in these types of reactions. This simplified the overall synthesis of acetylcholine because for methylation in the second step, methyl iodide can be added directly to the tritioacetylation reaction flask. The alcohol and N-tritioacetoxyphthalimide are present in about 1:1 ratio. The mixture is heated at about 70–80° C., preferably at 75° C., and maintained under inert conditions, such as under nitrogen or argon, for about 2 hours or longer, cooled to room temperature and an excess of methyl iodide, at least about 0.32 mmoles is injected. The mixture is stirred for 10 to about 60 minutes, the solvent and excess of methyl iodide is evaporated preferably under vacuum, deuteriated water is added and removed. Deuteriated water is then added again to the residue, the mixture is filtered and the resulting product is analyzed by $^1$H and $^3$H NMR spectroscopy.

$^1$H and $^3$H NMR spectroscopy confirmed that the synthesized compound was tritiated acetylcholine having specific activity of about 13 Ci/mmole. Depending on the specific activity of the tritiolabelling reagent and whether one, two or three tritiums are used, tritiated acetylcholine of specific activity from about 1 to 27, about 1 to 57.5 or 1 to 87 Ci/mmole can be prepared.

Thus, because of availability of novel acetylating agents, a much simplified chemical method for the synthesis of acetylcholine iodide was developed.

Example 1

Materials and Methods

This example describes general methods used for analysis of products obtained and materials used for preparation of the tritiolabelling reagents of the invention.

Deuterium gas (99.7%) was purchased from Liquid Carbonic, San Carlos, Calif. Tritium gas (97.9%) was obtained from the Savannah River Site. All other starting materials and reagents were purchased from Aldrich Chemical Co., St. Louis, Mo. Chemicals were used without further purification, except that tetrahydrofuran was freshly distilled from sodium and stored under dry nitrogen.

The tritium content of samples was analyzed on a Packard 1500 liquid scintillation counter, using Opti-Fluor™ cocktail.

Mass spectra of deuterated products were measured with a VG Prospec mass spectrometer, operating at 70 eV. All mass spectrometric analyses were carried out by the Analytical Laboratory, College of Chemistry, University of California, Berkeley. Mass spectra were corrected for fragmentation and isotope corrected as part of the % D calculations.

Analytical HPLC was performed on a Chem Pak silica column. The mobile phase was hexane:ether (75:25) for the N-tritioacetoxyphthalimide. HPLC analyses for peptides were performed on a LC-18 Vydac column, using a mobile phase of acetonitrile/water with 0.1% TFA from 2 to 52% gradient acetonitrile (1 to 26 min) and flow rate of 1.5 mL/min.

Preparative HPLC for $^3$H-acetyl Co—A was performed on a LC-18 Vydac column (0.5×24 cm), using solutions A and B. Solution A (0.2 M KHPO$_4$, pH 5) and solution B (20% acetonitrile in KHPO$_4$, pH 5) were used as mobile phases with 0 to 10 min isocratic (85% A: 15% B), and 10 to 45 min linear gradient (15% B to 50% B), and flow rate of 3 mL/min.

UV detection for peptide samples was at 234 and 210 nm on a Hewlett Packard 1040A diode array spectrophotometer, and radioactivity was monitored by an IN/US β-Ram™ HPLC flow detector, using a lithium glass scintillant cell with an efficiency of approximately 0.5%. The specific radioactivity of the reduction products was determined by comparison of standards with the analytical sample, combined with liquid scintillation counting of the isolated HPLC peak effluents.

Proton, deuterium and tritium NMR spectra were obtained on a Bruker AC-300 NMR spectrometer. $^1$H (300 MH$_z$) and $^3$H (320 MHz) spectra of products were recorded in a deuteriated solvent using a 5 mm $^3$H/$^1$H dual probe. $^2$H (46 MH$_z$) spectra were acquired on the lock channel of the same dual probe, with the analyte dissolved in the appropriate nondeuterated solvent.

Radioactive NMR samples were made to a volume of approximately 250 µL in teflon tubes, which were then placed inside 5 mm glass NMR tubes having a screw-cap. Referencing of tritium chemical shifts was achieved by generation of a ghost $^3$H TMS (tetramethylsilane) signal from internal TMS in the $^1$H NMR spectrum.

In the synthesis of tritiated acetyl Co-enzyme A, desalting of the tritiated product was performed on a Supelco LC-18

DB column (¼×24 Cm) with a flow rate of 1.5 mL/min. Solution A (50 mM NH$_4$OAc, pH 5 containing 2.5% acetonitrile) and solution B (100% acetonitrile) were used as mobile phases with 0 to 9 min isocratic (100% A), 9 to 10 min linear gradient (100% A to 100% B) and 10 to 20 min isocratic (100% B). UV detection was at 258 nm and the retention time was 14 minutes.

Example 2

Standards for Acetylation Reagents

This example describes synthesis of nonlabelled acetylation reagents.

N-Acetoxyphthalimide

N-acetoxyphthalimide was synthesized as follows:

N-hydroxyphthalimide (0.7 g, 4.35 mmole), acetic acid (HOAc, 258 μL, 4.35 mmol) and dicyclohexylcarbodiimide (DCC, 0.85 g, 4.35 mmol) were added to dry ethyl acetate (EtOAc, 125 mL), and the mixture was stirred for 3 hours at room temperature and filtered. The filtrate was dried (Na$_2$SO$_4$) and the residue was crystallized from ethanol to give a white solid (0.82 g, 90%), m.p. 185° C.

$^1$H NMR δ (CDCl$_3$) 7.76–7.89 (m, 4H), 2.39 (s, 3H).

N-acetoxysuccinimide

N-acetoxysuccinimide was prepared in the same manner as above, except that N-hydroxyphthalimide was substituted with N-hydroxysuccinimide.

N-Acetoxynaphthalimide

N-acetoxynaphthalimide was synthesized as follows:

The sodium salt of N-hydroxynaphthalimide (235 mg, 1 mmol) was suspended in benzene (5 mL) and a solution of acetyl chloride (0.08 mL, 1.14 mmol) in benzene (1 mL) was added dropwise. The reaction was vigorously stirred at room temperature, and after 5 minutes a white precipitate (NaCl) was formed. TLC of the reaction mixture (hexane:ethyl acetate 90:10) showed a new product (R$_f$ 0.7). The reaction mixture was filtered, and the solvent was evaporated under a stream of nitrogen gas to furnish a pale yellow product (234 mg, 91%), m.p. 205° C.

$^1$H NMR δ (CDCl$_3$) 8.64 (d, 2H), 8.29 (d, 2H), 7.79 (t, 2H), 2.47 (s, 3H).

Example 3

Synthesis of Bromo/Todo Precursors

This example describes synthesis of precursors for the labelled acetylation reagents.

N-Iodoacetoxyphthalimide

N-Hydroxyphthalimide (1.4 g, 8.7 mmol), iodoacetic acid (1.6 g, 8.7 mmol) and DCC (1.7 g, 8.7 mmol) were added to dry EtOAc (250 mL), and the mixture was stirred for 5 hours at room temperature. The reaction mixture was then filtered, the filtrate was dried, and the residue was crystallized from ethanol to give a white solid (2.15 g, 75%), m.p. 120° C.

$^1$H NMR δ (acetone-D$_6$) 8.01 (m, 4H), 4.32 (s, 2H).

Anal. Calculated C$_{10}$H$_6$NO$_4$I: C 36.2; H 1.8; I 38.4. Found: C 36.4; H 1.8; I 38.2.

N-Iodoacetoxysuccinimide

The synthesis of N-iodoacetoxysuccinimide is according to *J. Org. Chem.*, 30:448 (1965).

N-Hydroxysuccinimide (1 g, 8.7 mmole), iodoacetic acid (8.7 mmole, 1.6 g), and DCC (8.7 mmole, 1.7 g) were added to 250 mL of EtOAc and the mixture was stirred at room temperature for 5 hours. The mixture was filtered and the filtrate concentrated to dryness in vacuo. The residue was crystallized from ethanol to yield 1.74 g (71%) of white crystals, mp 148–150° C.

The infrared spectrum (Nujol) showed an ester carbonyl at 1740 cm$^{-1}$ and a lactam carbonyl at 1725 cm$^{-1}$.

Anal. Calculated (C$_6$H$_6$NO$_4$I): C: 25.44; H: 2.12; I: 44.87; Found: C: 25.12; H: 2.1; I: 44.35.

N-Iodoacetoxynaphthalimide

The sodium salt of N-hydroxynaphthalimide was acidified, and yielded two products, with the major component being the ring-opened product.

N-hydroxynaphthalimide (22 mg, 0.1 mmol), iodoacetic acid (18 mg, 0.1 mmol) and DCC (19.5 mg, 0.1 mmol) were added to dry EtOAc (2 mL), and the mixture was stirred for 5 hours at room temperature. The reaction mixture was then filtered, the filtrate was dried, and the residue was crystallized from ethanol to give a white solid (27 mg, 69%), m.p. 184° C.

$^1$H NMR δ (CDCl$_3$) 8.66 (d, 2H), 8.31 (d, 2H), 7.78 (t, 2H), 4.07 (s, 2H).

Anal. Calculated C$_{14}$H$_8$NO$_4$I: C: 44.1; H: 2.1; I: 33.3; Found: C: 44; H: 2.2; I: 33.8.

Example 4

Catalytic Dehalogenation With HT; N-Tritioacetoxysuccinimide Preparation

This example describes procedures used for labelling of precursors prepared in Example 3 by catalytic dehalogenation.

N-Tritioacetoxysuccinimide

N-Tritioacetoxysuccinimide was prepared as follows:

N-Iodoacetoxysuccinimide (14 mg, 0.05 mmol) was dissolved in EtOAc (1 mL), and Pd-C (10%, 10 mg) and triethylamine (4 μl) were added. The reaction vessel was connected to the vacuum line and the C—I bond was hydrogenolyzed under 1 atmosphere of 10% tritium gas for 2 hours. The reaction was then halted by removal of the tritium gas, methanol (1 mL) was added and removed by evacuation. The residue was dissolved in EtOAc (1 mL) and the catalyst was filtered off. EtOAc was removed and THF-D$_8$ (1 mL) was added for $^1$H and $^3$H NMR analyses. The total radioactivity was assessed by liquid scintillation counting as 10 mCi; the yield of radioactivity was 7.2%.

Results are seen in FIG. 2.

$^1$H NMR (THF-D$_8$) 2,23 (s, 3H), 2.71 (s, 4H).

[$^1$H]$^3$H NMR (THF-D$_8$) 2,24 (s, 50%), —O—CO—CH$_2$$^3$H), 4.05 (s, 50%, unknown).

N-Tritioacetoxynaphthalimide

N-Tritioacetoxynaphthalimide was prepared as follows:

N-Bromoacetoxynaphthalimide, prepared from bromoacetyl bromide and sodium N-hydroxynaphthalimide, (10.3 mg, 0.03 mmol) was dissolved in EtOAc (1 mL), and Pd-C (10%, 10 mg) and triethylamine (5 μL) were added. The reaction vessel was connected to a vacuum line and the compound was hydrogenolyzed under 1 atmosphere of 10% tritium gas for 2 hours. The reaction was then halted by removal of the tritium gas, methanol (1 mL) was added and removed by evacuation. EtOAc (1 mL) was added, the catalyst was removed by filtration and the product was analyzed by radio-HPLC to give 6.5 mg (85%) of N-tritioacetoxynaphthalimide having specific activity 1.6 Ci/mmole. Results are seen in FIG. 3.

$^1$H NMR δ (CDCl$_3$): 8.65 (d, 2H), 8.31 (d, 2H) 7.80 (t, 2H), 2.47 (s, 2.861).

[$^1$H]$^3$H NMR δ (CDCl$_3$): 2.47 (s); ($^1$H)$^3$H NMR δ (CDCl$_3$): 2.45 (t), J$_{HT}$=15.6 Hz.

Example 5

N-Tritioacetoxyphthalimide Preparation; Radical Dehalogenation (all reagents)

This example describes procedures used for labelling of acetylation reagents by radical dehalogenation. Compounds were labelled both with deuterium or with tritium.

For the tritiation reactions, high specific activity tributyltin tritide (TBT$^3$H) was prepared and used for the radical dehalogenation of the N-iodoacetoxyphthalimide or N-iodoacetoxy precursors. Using the tributyltin tritide reagent, several different batches of the tritioacetoxy reagent were prepared and the purity, yield and the specific activity of the reagents were investigated and confirmed by NMR and HPLC analyses. Originally, the desired tritioacetylating reagent was found to be present together with some tin by-products that were formed during the radical dehalogenation reaction. Therefore, the tritioacetylating reagent was purified and the tin by-products and impurities were removed by extracting the crude reaction mixture with an organic solvent, preferably with acetonitrile and hexane. N-deuterioacetoxysuccinimide, N-tritioacetoxysuccinimide and naphthalimide analogs are prepared in the same way.

N-Deuterioacetoxyphthalimide

N-Deuterioacetoxyphthalimide was prepared as follows:

A solution of N-iodoacetoxyphthalimide (10 mg, 0.03 mmol) in dry THF (0.3 mL) was added dropwise to a mixture of tributyltin deuteride (13 µL, 0.045 mmol) and triethyl borane (4 µL 0.004 mmol) in dry THF (0.7 mL) under a nitrogen atmosphere. The reaction was stirred at room temperature for 3 hours. After the reaction was complete, the solvent was removed under a flow of nitrogen gas and the residue was dissolved in acetonitrile (1 mL) and extracted with hexane (1 mL, 5×). The residue was analyzed by HPLC to give (2.36 mg, 38%), m.p. 190° C.; m/z 206($^2$H-60%).

N-Tritioacetoxyphthalimide (First batch)

N-Tritioacetoxyphthalimide was prepared as follows:

N-Iodoacetoxyphthalimide (20 mg, 0.06 mmol) was dissolved in dry THF (0.6 mL) and the solution was added to a solution of previously prepared tributyltin tritide (0.09 mmol) and triethyl borane (8 µL, 0.008 mmol) in dry THF (1.4 mL) under N$_2$. The reaction was then stirred at room temperature for 3 hrs, the solvent was removed under vacuum and the flask was filled with nitrogen gas. The crude reaction mixture was extracted with hexane (1 mL, 5×) and the residue was dissolved in deuteriated acetonitrile (1 mL). Radio-HPLC analysis showed 40% yield of the desired product with a specific activity of 18 Ci/mmole.

FIG. 5 shows NMR spectra of N-tritioacetoxyphthalimide and N-tritioacetyl-ACTH. Specifically, FIG. 5A shows the 320 MH$_z$ $^3$H NMR spectrum of N-tritioacetoxyphthalimide in acetonitrile-D$_3$ (δ2.00–2.70 ppm), FIG. 5B shows the 320 MH$_z$ $^1$H decoupled $^3$H NMR spectrum of N-tritioacetoxyphthalimide, FIG. 5C shows the 300 MH$_z$ $^1$H NMR spectrum of N-tritioacetoxyphthalimide and FIG. 5D shows 320 MH$_z$ $^1$H decoupled $^3$H NMR spectrum of N-tritioacetyl-ACTH in D$_2$O (δ1.70–2.40 ppm).

As seen in FIG. 5A, the proton ($^1$H) coupled tritium ($^3$H) NMR spectrum of the purified N-tritoacetoxyphthalimide shows a triplet at 2.36 ppm for the tritioacetoxy (J$_{HT}$ 15.6 Hz), which collapsed to a singlet in the proton decoupled tritium spectrum, as seen in FIG. 5B. The proton $^1$H NMR spectrum of the tritiated sample shows a singlet for the —CH$_3$ species at 2.37 ppm and a doublet for the —CH$_2$$^3$H species at 2.33 ppm. The downfield line of the doublet is obscured by the —CH$_3$ singlet, as seen in FIG. 5C. Integration of the methyl peaks in this proton spectrum of the tritiated sample allowed calculation of the specific activity of the N-tritioacetoxyphthalimide at 18 Ci/mmole, which was found to be in agreement with HPLC analyses.

N-Deuterioacetoxynaphthalimide

N-Deuterioacetoxynaphthalimide was prepared as follows:

N-Iodoacetoxynaphthalimide (10 mg, 0.026 mmol) was dissolved in dry THF (0.3 mL) and the mixture was added dropwise to a solution of tributyltin deuteride (13 µL, 0.045 mmole) and triethyl borane (4 µL, 0.004 mmol) in dry THF (0.7 mL) under nitrogen. After the reaction was stirred at room temperature for 4 hours, monitoring by TLC (hexane:ethyl acetate 5:1) showed only 10–20% product. The reaction was continued for an additional 12 hours, after which the solvent was removed under a flow of nitrogen and the residue was dissolved in CDCl$_3$ for $^1$H NMR analysis. The ratio of the product to starting material was estimated to be approximately 80%:20%.

$^1$H NMR δ (CDCl$_3$) 8.66 (d, 2H), 8.31 (d, 2H), 7.78 (t, 2H), 2.47 (s, 2H); m/z 256 ($^2$H-64%).

N-Tritioacetoxynaphthalimide

N-Tritioacetoxynaphthalimide is prepared using the same conditions as described for N-deuterioacetoxynaphthalimide, except that the tributyltin deuteride is substituted with tributyltin tritide.

Example 6

Second N-Tritioacetoxyphthalimide Preparation

This example describes an alternate preparation of N-tritioacetoxyphthalimide (second batch).

N-Iodoacetoxyphthalimide (33 mg, 0.1 mmole) was dissolved in dry THF (0.3 mL) and added to a solution of previously prepared tritiated tributyltin (0.135 mmole), TEB (12 µL, 0.014 mmole) in dry THF (0.7 mL) under N$_2$. The reaction was then stirred at room temperature for 3 hours and the solvent was removed under vacuum and the flask was filled with nitrogen gas. The crude reaction was dissolved in acetonitrile (1.5 mL) and extracted with hexane (1.5 mL, 5×5) to remove the organotin impurities. The acetonitrile was removed under nitrogen and deuteriated acetonitrile (1 mL) was added for the total radioactivity, proton and triton NMR analyses. The specific activity of the N-tritioacetoxyphthalimide reagent was determined to be 13 Ci/mmole by $^3$H NMR analysis. Results are seen and described in FIG. 5. [$^1$H] H NMR δ (CD$_3$CN) 2.36 (s), ($^1$H)$^3$H NMR 2.35 (t), J$_{HT}$=15.6 Hz.

Example 7

Fluoride-Induced Desilylation Reaction

This example describes an alternative method for preparation of N-tritioacetoxyphthalimide reagent.

THF and ether were dried using lithium aluminum hydride (LAH) prior to the experiment.

Trimethylsilylacetic acid (0.1 mmole) and N-hydroxyphthalimide (0.1 mmole) were weighed under N$_2$ and placed in a conical flask with 2 side arms (flask A). Dry THF/dioxane (0.5 mL) was added and removed carefully under vacuum to dry the substrates. THF (0.4 mL) was added and mixed to dissolve the substrates. DCC (95 µL, 1 M solution in methylene chloride) dried on activated molecular sieves was added and mixed. The reaction was stirred 3 hours, and a precipitate formed after 10 minutes. THF was removed under vacuum to dryness. Dry ether was added (1 mL) and mixed to dissolve the product of coupling, the reaction was left for 5 minutes for the by-product dicyclohexylurea to settle. The upper layer was transferred and filtered into the second flask. Dry ether (0.5 mL) was added, mixed and the upper layer was again transferred as above. The ether was removed under vacuum to leave the TMS-acetoxyphthalimide as a white solid.

$T_2O$ [0.2 mmole from $PtO_2$(28 mg) and $T_2$] in dry THF (0.5 mL) was added to the second flask. The mixture was rinsed with THF (0.25 mL). Dried CsF (0.1 mmole) was dropped from a spoon into the reaction mixture and the mixture was stirred. After 30 minutes the solvent was removed under high vacuum. Dry THF (0.5 mL) was added and evaporated to remove the residual tritiated water. The reaction flask was transferred to the work-up box to be filtered and analyzed.

The resulting N-tritioacetoxyphthalimide had a specific activity of 12.5 Ci/mmole; yield 51%.

Example 8

General Acetylation of Peptides

This example describes general procedures used for N-tritioacetylation of peptides.

Freshly prepared N-tritioacetoxyphthalimide (0.58 mg. 2.8 µmol, 16.8 Ci/mmole) was dissolved in EtOAc or acetonitrile (250 µL). This solution was added to a peptide (2 µmole) dissolved in DMSO (250 µL) and triethylamine (5 µL). The mixture was vortexed at room temperature for 1 hour. A slight yellow to orange color was observed after the reaction was finished. The solvents were removed by lyophilization, and the residue was dissolved in deuteriated water (300 µL), filtered, and the filtrate was analyzed by radio-HPLC and tritium NMR spectroscopy. The reaction afforded about 30% yield of tritiolabelled peptide of S. A. 16.8 Ci/mmole.

Example 9

General Acetylation of HMP-Peptides

This example describes a general procedure used for N-tritioacetylation of hydroxymethyl polystyrene (HMP) bound peptides.

A six amino acid peptide (8.3 mg, 3.96 µmol) was suspended in DMSO (100 µL) in a conical vial and triethylamine (2 µL) was added. N-Tritioacetoxyphthalimide (18 Ci/mmole, 1.2 mg, 5.7 µmol) in EtOAc (100 µL) was prepared and added to the HMP-peptide in DMSO. The reaction vessel was vortexed at room temperature for 30 min. The supernatant (200 µL) was separated and the residue was then centrifuged at 15,000 g for 2 min. and washed and centrifuged alternately with N-methylpyrrolidine (0.5 mL) and dichloromethane:methanol (1:1, 0.5 mL) for a total of 6 washes. The residue was lyophilized for 10 minutes and the N-[$^3$H]-acetylated peptide was deprotected and released from the resin by the addition of thioanisole (10 µL), ethanedithiol (10 µL) and trifluoroacetic acid (80 µL). The mixture was vortexed for 2 hours. Water (0.5 mL) was added and the vial was centrifuged to separate the resin. The supernatant was removed and the pellet was washed by the addition of water (0.5 mL). The combined supernatant was lyophilized overnight. The resultant peptide was dissolved in deuteriated water (0.3 mL) and purified by HPLC to give the desired radiochemically pure peptide with a specific activity of 18 Ci/mmole and chemical yield of 35%.

[$^1$H]$^3$H NMR δ ($D_2O$) 2.04 (s), ($^1$H)$^3$H NMR δ ($D_2O$) 2.06 (t).

Example 10

Preparation of Acetyl Co—A

This example describes preparation of acetyl Co—A using the N-acetoxyphthalimide reagent.

Co-enzyme A sodium salt (10 mg, 0.011 mmole) was dissolved in water (0.5 mL) and TEA (14 µL, 0.1 mmole) was added and mixed. A solution of N-acetoxyphthalimide (2.66 mg, 0.013 mmole) in acetonitrile (540 µL) was added from a stock solution to the Co—A solution and the mixture was vortexed for 1 hour at room temperature. The color of the solution was slightly yellow indicating that the reaction was complete. The solution was filtered and the filter was washed with 200 µL water and the solvent was removed under vacuum. $D_2O$ (1 mL) was added to the residue and the solution was filtered through glass wool. The product was analyzed by HPLC and $^1$H NMR spectroscopic analysis. HPLC analysis showed a chemical yield of 8.18 mg (80%).

$^1$H NMR δ ($D_2O$) 8.59 (s, 1H, C8-H), 8.28 (s, 1H, C2-H), 6.20 (m, 1H C1'-H), 4.80–4.92 (m, 1H, C240 -H), 4.60 (m, 1H, C3'-H), 4.23 (m, 1H, C4'-H) 3.97 (s, 1H), 3.82–3.87 (t, $CH_2$), 3.30–3.34 (m, 2H C5'-H), 2.94 (t, $CH_2$), 2.41 (t, $CH_2$), 2.23 (s, CO-$CH_3$), 0.9 (s, $CH_3$), 0.77 (s, $CH_3$).

Example 11

Preparation of [$^3$H] Acetyl Co—A

This example describes preparation of [$^3$H]acetyl-CoA using the N-tritioacetoxyphthalimide reagent.

Co-enzyme A sodium salt (10 mg, 0.011 mmole) was dissolved in water (0.5 mL) and TEA (14 µL, 0.1 mmole) was added and mixed. A solution of N-tritioacetoxyphthalimide (0.013 mmole, 218 mCi, having a specific activity 18 Ci/mmole) in acetonitrile (540 µL) was added from a stock solution to the Co—A solution and the mixture was vortexed for 1 hour at room temperature. The color of the solution was yellow. The solution was filtered and the filter was rinsed with 200 µL water and the solvents were removed under vacuum. $D_2O$ (700 µL) was added to the residue and the mixture was analyzed for total radioactivity which was found to be approximately 160 mCi.

The crude product was analyzed by $^1$H and $^3$H NMR spectroscopy to show a peak at 2.36 ppm and was then purified and desalted by a HPLC method (36% yield) for final tritium NMR analysis. The resulting acetyl Co—A was found to have a specific activity of 14.4 Ci/mmole.

δH NMR δ ($D_2O$) 8.59 9s, 1H, C8-H), 8.28 (s, 1H, C2-H), 6.20 (m, 1H, C1'-H), 4.80–4.92 (m, 1H, C2'-H), 4.60 (m, 1H, C3'-H), 4.23 (m, 1H, C4'-H) 3.97 (s, 1H), 3.82–3.87 (t, $CH_2$), 3.30–3.34 (m, 2H C5'-H), 2.94 (t, $CH_2$), 2.41 (t, $CH_2$), 2.33 (s, $CH_2$T), 0.9 (s, $CH_3$), 0.77 (s, $CH_3$). [3H] NMR 2.35 (t), $J_{HT}$=15.6 Hz.

Example 12

Preparation of [$^3$H] Acetylcholine Iodide

This example describes chemical synthesis of high specific activity [$^3$H] acetylcholine iodide.

N,N-Dimethylaminoethanol (4 µL, 0.04 mmole) was dissolved in dry acetonitrile (0.25 mL) and was placed in a reaction vessel connected to the vacuum line. N-tritioacetoxyphthalimide (0.04 mmole, specific activity 13 Ci/mmole) in dry acetonitrile (0.8 mL) was then added through the side-arm of the reaction vessel. The mixture was heated at 75° C. for 2 hours under $N_2$, then brought to room temperature and methyl iodide (20 μL) was injected. The mixture was stirred for 1 hour. The solvent and excess of methyl iodide was evaporated under vacuum. Deuterated water (0.5 mL) was added and removed. $D_2O$ (1 mL) was then added to the residue and filtered and the product was analyzed by $^1H$ and $^3H$ NMR spectroscopy.

$^3H$ NMR δ ($D_2O$) $^1H$ decoupled 2.05(s), $^1H$ coupled, 2.05 (t). Specific activity found was 13 Ci/mmole.

Example 13

Synthesis of N-Ditritio and N-Tritritio Reagents

This example describes procedures used for synthesis of N-ditritio and N-tritritioacetylating reagents.

N-Ditritioacetoxyphthalimide

Dibromoacetic acid (0.1 mmole) and N-hydroxyphthalimide (0.1 mmole) are mixed and coupled in THF in the presence of DCC for 2 hours. The product, (N-dibromoacetoxyphthalimide) is isolated by filtration and dried. Radical-induced dehalogenation (0.1 mmole scale) using the general method with tributyltin deuteride furnished the N-deuterioacetoxyphthalimide with two atoms of deuterium. The N-ditritioacetoxyphthalimide can be prepared the same way.

N-Tritritioacetoxyphthalimide

High specific activity tritiated methyl iodide is used. A Grignard reagent, methyl magnesium iodide, is prepared and reacted with carbon dioxide. The high specific activity tritiated acetic acid derivative is formed and is then released as the free acid. The tritiated acetic acid is coupled with N-hydroxyphthalimide in the presence of DCC to form the high specific activity N-tritritioacetoxyphthalimide. This method furnishes the reagent with three tritium atoms at a specific activity of about 87 Ci/mmole.

What is claimed:

1. A tritioacetylating reagent of a specific activity of about 1 to about 87 Ci/mmole selected from the group consisting of N-tritioacetoxyphthalimide, N-tritioacetoxysuccinimide and N-tritioacetoxynaphthalimide, N-ditritioacetoxyphthalimide, N-ditritioacetoxysuccinimide, N-ditritioacetoxynaphthalimide, N-tritritioacetoxyphthalimide, N-tritritioacetoxysuccinimide, N-tritritioacetoxynaphthalimide.

2. The reagent of claim 1 wherein the specific activity of the reagent is from about 1 to about 57 Ci/mmole.

3. The reagent of claim 2 wherein the specific activity is from about 1–28 Ci/mmole.

4. The reagent of claim 3, namely N-tritioacetoxyphthalimide.

5. The reagent of claim 3, namely N-tritioacetoxysuccinimide.

6. The reagent of claim 3, namely N-tritioacetoxynaphthalimide.

7. A radical dehalogenation method for preparation of N-tritioacetylating reagent, said method comprising steps:
(a) preparing a haloacetoxy precursor of N-acetoxyphthalimide, N-acetoxysuccinimide or N-acetoxynaphthalimide;
(b) reacting said precursor with tributyltin tritide and triethyl borane in the presence of an organic solvent.

8. The method of claim 7 wherein said haloacetoxy precursor is selected from the group consisting of N-iodoacetoxyphthalimide, N-bromoacetoxyphthalimide, N-iodoacetoxysuccinimide, N-bromoacetoxysuccinimide, N-iodoacetoxynaphthalimide and N-bromoacetoxynaphthalimide.

9. The method of claim 8, wherein said haloacetoxy precursor is prepared by reacting N-hydroxyphthalimide, N-hydroxysuccinimide or N-hydroxynaphthalimide with haloacetic acid in the presence dicyclohexylcarbodiimide and an organic solvent.

10. The method of claim 9, wherein the organic solvent in the step (b) of claim 9 is dry tetrahydrofuran and wherein tributyltin tritide has a specific activity about 28.7 Ci/mmole.

11. A method for preparation of acetylcholine by acetylation of choline using an acetylating reagent selected from the group consisting of N-acetoxyphthalimide, N-acetoxysuccinimide and N-acetoxynaphthalimide, said method comprising steps:
(a) acetylating N,N-dimethylaminoethanol with the acetylating agent in an organic solvent selected from the group consisting of acetonitrile, tetrahydrofuran, ethyl acetate and acetone in the presence of an organic base at a temperature of about 25° C.; and
(b) adding methyl iodide to a reaction mixture of step (a).

12. The method of claim 11 wherein the acetylating reagent is N-acetoxyphthalimide and the organic base is triethylamine.

13. The method of claim 11 wherein the acetylating reagent is N-acetoxysuccinimide and the organic base is triethylamine.

14. The method of claim 11 wherein the acetylating reagent is N-acetoxynaphthalimide and the organic base is triethylamine.

15. A method for preparation of tritiated acetylcholine by acetylation of choline using a tritioacetylating reagent, selected from the group consisting of N-tritioacetoxyphthalimide, N-tritioacetoxysuccinimide and N-tritioacetoxynaphthalimide, having a specific activity from about 1 to about 87 Ci/mmole, said method comprising steps:
(a) acetylating N,N-dimethylaminoethanol with the tritioacetylating agent in an organic solvent selected from the group consisting of acetonitrile, tetrahydrofuran and acetone in the presence of an organic base at a temperature of about 25° C.; and
(b) adding methyl iodide to a reaction mixture of step (a).

16. The method of claim 15 wherein the specific activity of the tritiolabelling reagent is from about 5 to about 57 Ci/mmole.

17. The method of claim 16 wherein the specific activity of the tritiolabelling reagent is from about 5 to about 27 Ci/mmole.

18. The method of claim 16 wherein the acetylating reagent is N-tritioacetoxyphthalimide.

19. The method of claim 16 wherein the acetylating reagent is N-tritioacetoxysuccinimide.

20. The method of claim 16 wherein the acetylating reagent is N-tritioacetoxynaphthalimide.

21. A method for preparation of acetyl Co—A by acetylation of coenzyme A using an acetylating reagent selected from the group consisting of N-acetoxyphthalimide, N-acetoxysuccinimide and N-acetoxynaphthalimide, said method comprising of:
(a) subjecting coenzyme A to acetylation by mixing the acetylating reagent with coenzyme A in an organic solvent selected from the group consisting of acetonitrile, ethyl acetate, acetone, dioxane and tetrahydrofuran in the presence of an organic base and water.

22. The method of claim 21 wherein the acetylating reagent is N-acetoxyphthalimide and the organic base is triethylamine.

23. The method of claim 21 wherein the acetylating reagent is N-acetoxysuccinimide and the organic base is triethylamine.

24. The method of claim 21 wherein the acetylating reagent is N-acetoxynaphthalimide and the organic base is triethylamine.

25. A method for preparation of tritiated acetyl Co—A by acetylation of coenzyme A using a tritioacetylating reagent selected from the group consisting of N-tritioacetoxyphthalimide, N-tritioacetoxynaphthalimide and N-tritioacetoxysuccinimide, having a specific activity from about 1 to about 87 Ci/mmole, said method comprising of:

(a) subjecting coenzyme A to acetylation by mixing the acetylating reagent with coenzyme A in water and an organic solvent selected from the group consisting of acetonitrile, acetone and tetrahydrofuran in the presence of an organic base.

26. The method of claim 25 wherein the specific activity of the tritioacetylating agent is from about 1 to about 87 Ci/mmole.

27. The method of claim 26 wherein the specific activity of the tritioacetylating agent is from about 5 to about 27 Ci/mmole.

28. The method of claim 26 wherein the acetylating reagent is N-tritioacetoxyphthalimide.

29. The method of claim 26 wherein the acetylating reagent is N-tritioacetoxynaphthalimide.

30. The method of claim 26 wherein the acetylating reagent is N-tritioacetoxysuccinimide.

31. A method for tritiation of organic compounds containing a free —$NH_2$, —SH or —OH group with a tritium content from 1–87 Ci/mmole, said method comprising steps:

(a) contacting the organic compound with a N-tritioacetoxy reagent selected from the group consisting of N-tritioacetoxyphthalimide, N-tritioacetoxysuccinimide and N-tritioacetoxynaphthalimide, N-ditritioacetoxyphthalimide, N-ditritioacetoxysuccinimide, N-ditritioacetoxynaphthalimide, N-tritritioacetoxyphthalimide, N-tritritioacetoxysuccinimide and N-tritritioacetoxynaphthalimide.

32. An acetylating reagent for acetylation of organic compounds containing free —$NH_2$, —SH or —OH group, wherein said acetylating agent is N-acetoxynaphthalimide characterized by:

melting point: 205° C.; mass spectrum: m/z=255;

NMR spectra: $^1$H NMR delta ($CDCl_3$) 8.64 (d, 2H), 8.29 (d, 2H), 7.79 (t, 2H), 2.47 (s, 3H); and wherein said organic compound is an amine, amino acid or a peptide.

33. The reagent of claim 32, wherein the amino acid is L-cysteine or muramic acid and amine is benzylamine.

34. The reagent of claim 32, wherein the organic compound is choline or coenzyme A.

* * * * *

UNITED STATES PATENT AND TRADEMARK OFFICE
CERTIFICATE OF CORRECTION

PATENT NO. : 6,160,128
DATED : December 12, 2000
INVENTOR(S) : Manouchehr Saljoughian, et al.

It is certified that error appears in the above-identified patent and that said Letters Patent is hereby corrected as shown below:

<u>Title page, Inventors,</u>
Delete "Manoucher" and insert -- Manouchehr --;

<u>Column 6, Scheme 2,</u>
Delete

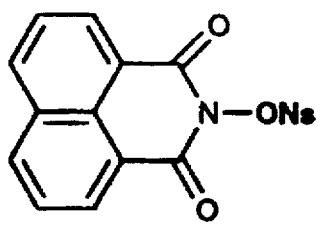

And insert

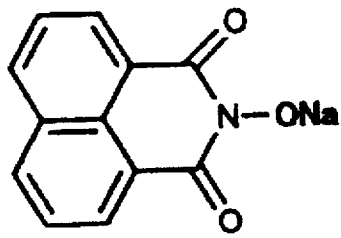

<u>Column 21,</u>
Line 47, delete "Todo" and insert -- Iodo --.

Signed and Sealed this

Twenty-third Day of October, 2001

Attest:

NICHOLAS P. GODICI
Attesting Officer   Acting Director of the United States Patent and Trademark Office